US010639230B2

(12) United States Patent
Le et al.

(10) Patent No.: US 10,639,230 B2
(45) Date of Patent: May 5, 2020

(54) MASSAGE CHAIR HAVING A MECHANISM FOR ADJUSTING POSITION OF FLUID MASSAGE ELEMENT FOR ARM MASSAGING

(71) Applicants: Kevin Le, Richland Hills, TX (US); Thanh Le, Grand Prairie, TX (US); Abhishek Vinod Vazrekar, Arlington, TX (US); Varad Nitin Gokhale, Irving, TX (US)

(72) Inventors: Kevin Le, Richland Hills, TX (US); Thanh Le, Grand Prairie, TX (US); Abhishek Vinod Vazrekar, Arlington, TX (US); Varad Nitin Gokhale, Irving, TX (US)

(73) Assignee: Luraco, Inc., Arlington, TX (US)

( * ) Notice: Subject to any disclaimer, the term of this patent is extended or adjusted under 35 U.S.C. 154(b) by 0 days.

(21) Appl. No.: 15/965,955

(22) Filed: Apr. 29, 2018

(65) Prior Publication Data

US 2019/0328608 A1    Oct. 31, 2019

(51) Int. Cl.
*A61H 9/00* (2006.01)
*A61H 15/00* (2006.01)

(52) U.S. Cl.
CPC . *A61H 15/0078* (2013.01); *A61H 2201/0149* (2013.01); *A61H 2205/06* (2013.01);
(Continued)

(58) Field of Classification Search
CPC ........ A61H 9/00; A61H 9/005; A61H 9/0078; A61H 2201/0134; A61H 2201/0149
(Continued)

(56) References Cited

U.S. PATENT DOCUMENTS 2,817,524 A * 12/1957 Sadler ................ A63B 21/4049
482/117
3,483,862 A * 12/1969 Takeuchi ............... A61H 39/04
297/396
(Continued)

FOREIGN PATENT DOCUMENTS

CN       1446529 A    12/2002
CN     100398081 C     7/2008
(Continued)

OTHER PUBLICATIONS

"MassageChairStore.com," downloaded Sep. 12, 2013, <URL:http://www.massagechairstore.com/>.
(Continued)

*Primary Examiner* — Justine R Yu
*Assistant Examiner* — Christopher E Miller
(74) *Attorney, Agent, or Firm* — Hoang Steve Ngo

(57) ABSTRACT

The present invention is a massage chair having a mechanism for adjusting position of massage element for arm massaging. As a non-limiting example, the massage chair preferably includes a massage chair frame; at least one arm massager apparatus positioned about a corresponding side of the frame; and a mechanism for securing the at least one arm massager apparatus about a corresponding side of the frame. In this example, the arm massage system may include at least one massage element for hand massaging, at least one massage element for tricep massaging, at least one massage element for shoulder massaging, a mechanism for adjusting position of the massage element for tricep massaging, and a mechanism for adjusting position of the massage element for shoulder massaging. The massage chair may further include a body massage system; a legs and feet massage system; and a noise-reducing, enclosure device.

54 Claims, 35 Drawing Sheets

(52) U.S. Cl.
CPC .. *A61H 2205/081* (2013.01); *A61H 2205/106* (2013.01); *A61H 2205/108* (2013.01); *A61H 2205/12* (2013.01)

(58) Field of Classification Search
USPC .......................................... 248/118.3, 285.1
See application file for complete search history.

(56) References Cited

U.S. PATENT DOCUMENTS

| | | | |
|---|---|---|---|
| 4,422,448 A | 12/1983 | Sugai et al. | |
| 4,422,449 A | 12/1983 | Hamabe | |
| 4,574,786 A | 3/1986 | Hashimoto et al. | |
| 5,020,518 A | 6/1991 | Spears et al. | |
| 5,074,501 A * | 12/1991 | Holtta ................ | B43L 15/00 248/118.3 |
| 5,233,973 A | 8/1993 | Gill et al. | |
| 5,281,001 A * | 1/1994 | Bergsten ............ | A47B 21/0371 248/118 |
| 5,304,112 A | 4/1994 | Mrklas et al. | |
| 5,405,109 A * | 4/1995 | Nordnes ............ | A47B 21/0371 248/118.3 |
| 5,769,799 A | 6/1998 | Daughtry | |
| 5,876,359 A * | 3/1999 | Bock .................... | A61H 9/0078 601/150 |
| 6,056,707 A * | 5/2000 | Hayashi ................ | A47C 3/02 601/100 |
| 6,171,266 B1 | 1/2001 | Inada et al. | |
| 6,224,563 B1 | 5/2001 | Nonoue et al. | |
| 6,312,400 B1 * | 11/2001 | Itikawa ................ | A61H 7/004 601/100 |
| 6,394,970 B1 | 5/2002 | Maier | |
| 6,491,652 B1 * | 12/2002 | Hata .................... | A61H 9/0078 601/148 |
| 6,494,850 B1 | 12/2002 | Kitadou et al. | |
| 6,511,448 B1 | 1/2003 | Furuie et al. | |
| 6,540,701 B1 | 4/2003 | Inada | |
| 6,619,747 B2 * | 9/2003 | Ko .......................... | A47C 7/54 248/118.3 |
| 6,629,939 B2 | 10/2003 | Jikiba et al. | |
| 6,629,944 B2 * | 10/2003 | Smart ...................... | A61F 5/04 128/845 |
| 6,656,140 B2 | 12/2003 | Oguma et al. | |
| 6,695,799 B2 | 2/2004 | Kitadou et al. | |
| 6,749,577 B2 | 6/2004 | Kume et al. | |
| 6,773,071 B1 * | 8/2004 | Stasney ................ | A47C 7/546 248/118.3 |
| 6,786,461 B1 * | 9/2004 | Tsai .................... | A47B 21/0371 248/118.3 |
| 6,899,687 B2 | 5/2005 | Hori et al. | |
| 6,923,505 B2 * | 8/2005 | Siminovitch ............ | A47C 7/54 248/118.1 |
| 6,991,609 B2 | 1/2006 | Kan et al. | |
| 7,222,826 B1 * | 5/2007 | Berglund ............ | A47B 21/0314 248/118 |
| 7,806,840 B2 | 10/2010 | Chen | |
| 7,854,710 B2 | 12/2010 | Liang | |
| 7,947,002 B2 | 5/2011 | Mizoguchi et al. | |
| 2002/0130226 A1 * | 9/2002 | Nogueira ............ | A47B 21/0371 248/118.5 |
| 2002/0138023 A1 | 9/2002 | Kume et al. | |
| 2002/0193713 A1 | 12/2002 | Lee | |
| 2004/0097854 A1 * | 5/2004 | Hester .................... | A61H 23/04 601/149 |
| 2004/0122343 A1 | 6/2004 | Mori et al. | |
| 2004/0158181 A1 | 8/2004 | Watanabe et al. | |
| 2005/0090769 A1 | 4/2005 | Chen | |
| 2005/0146176 A1 * | 7/2005 | Yoda .................... | A61H 9/0071 297/217.1 |
| 2005/0192520 A1 | 9/2005 | Morita et al. | |
| 2005/0242635 A1 | 11/2005 | Cassaday | |
| 2006/0087097 A1 * | 4/2006 | Kramer .................. | A47C 7/62 280/304.1 |
| 2006/0111653 A1 | 5/2006 | Nishio et al. | |
| 2006/0142676 A1 * | 6/2006 | Fujii .................... | A61H 9/0078 601/98 |
| 2006/0217643 A1 * | 9/2006 | Yonekawa ........... | A61H 9/0078 601/148 |
| 2007/0010767 A1 * | 1/2007 | Hsieh .................... | A61H 9/0078 601/96 |
| 2007/0016119 A1 * | 1/2007 | Inada .................... | A61H 9/0078 601/151 |
| 2007/0225624 A1 * | 9/2007 | Tsukada ............. | A61H 15/0078 601/49 |
| 2007/0239089 A1 | 10/2007 | Chiu | |
| 2007/0287941 A1 * | 12/2007 | Yoda .................... | A61H 9/0078 601/151 |
| 2007/0299377 A1 | 12/2007 | Shiraishi | |
| 2008/0009777 A1 | 1/2008 | Chiu | |
| 2008/0097260 A1 | 4/2008 | Tsukada et al. | |
| 2009/0260639 A1 * | 10/2009 | Hsu .................... | A61G 7/05769 128/888 |
| 2009/0306555 A1 * | 12/2009 | Goto ........................ | A61H 5/00 601/15 |
| 2009/0306558 A1 | 12/2009 | Chen | |
| 2010/0030121 A1 | 2/2010 | Fu | |
| 2010/0198120 A1 * | 8/2010 | Tago .................... | A61H 1/0237 601/134 |
| 2010/0198121 A1 * | 8/2010 | Tago .................... | A61H 9/0078 601/150 |
| 2010/0312155 A1 * | 12/2010 | Fukuyama ........... | A61H 9/0078 601/98 |
| 2011/0015554 A1 * | 1/2011 | Morikawa ........... | A61H 1/0244 601/84 |
| 2011/0077561 A1 | 3/2011 | Choly | |
| 2012/0071799 A1 * | 3/2012 | Inada .................... | A61H 7/004 601/98 |
| 2012/0157899 A1 * | 6/2012 | Terada ................. | A61H 9/0078 601/149 |
| 2012/0215143 A1 * | 8/2012 | Inada .................... | A61H 1/003 601/112 |
| 2013/0088059 A1 * | 4/2013 | Nagamitsu ............. | A61H 1/003 297/260.2 |
| 2014/0343467 A1 * | 11/2014 | Fukuyama ............. | A61H 7/007 601/98 |
| 2015/0051526 A1 | 2/2015 | Wang et al. | |
| 2015/0157528 A1 * | 6/2015 | Le .......................... | A61H 15/00 601/99 |
| 2015/0351997 A1 * | 12/2015 | Le ....................... | A61H 9/0078 601/150 |
| 2015/0366746 A1 * | 12/2015 | Ashby ................ | A61H 15/0078 601/49 |
| 2016/0106620 A1 * | 4/2016 | Uno .................... | A61H 9/0078 601/149 |
| 2016/0229320 A1 * | 8/2016 | Lem ...................... | B60N 2/448 |
| 2016/0324717 A1 * | 11/2016 | Burton .................. | A61H 7/001 |
| 2017/0056280 A1 * | 3/2017 | Ode ..................... | A61H 9/0078 |

FOREIGN PATENT DOCUMENTS

| | | |
|---|---|---|
| CN | 101744707 B | 10/2011 |
| EP | 1230904 A2 | 8/2002 |
| EP | 1210927 B1 | 1/2005 |
| JP | H06209 A | 1/1994 |
| JP | H1119150 A | 1/1999 |
| WO | WO-2009013870 A1 * | 1/2009 |

OTHER PUBLICATIONS

"How Massage Chairs Work," downloaded Sep. 12, 2013, <URL:http://electronics.howstuffworks.com/gadgets/home/massage-chair1.htm>.
"Osaki OS-4000 Instruction Manual," downloaded Sep. 12, 2013, <URL:http://www.hitechmassagechairs.com/PDF/OS-4000-Manual.pdf>.
"luminous-spa-pedicure-chair-owner-manual," downloaded Aug. 15, 2016, <URL:http://uspedicurespa.com/resources/lexor/luminous-spa-pedicure-chair-owner-manual.pdf>.

* cited by examiner

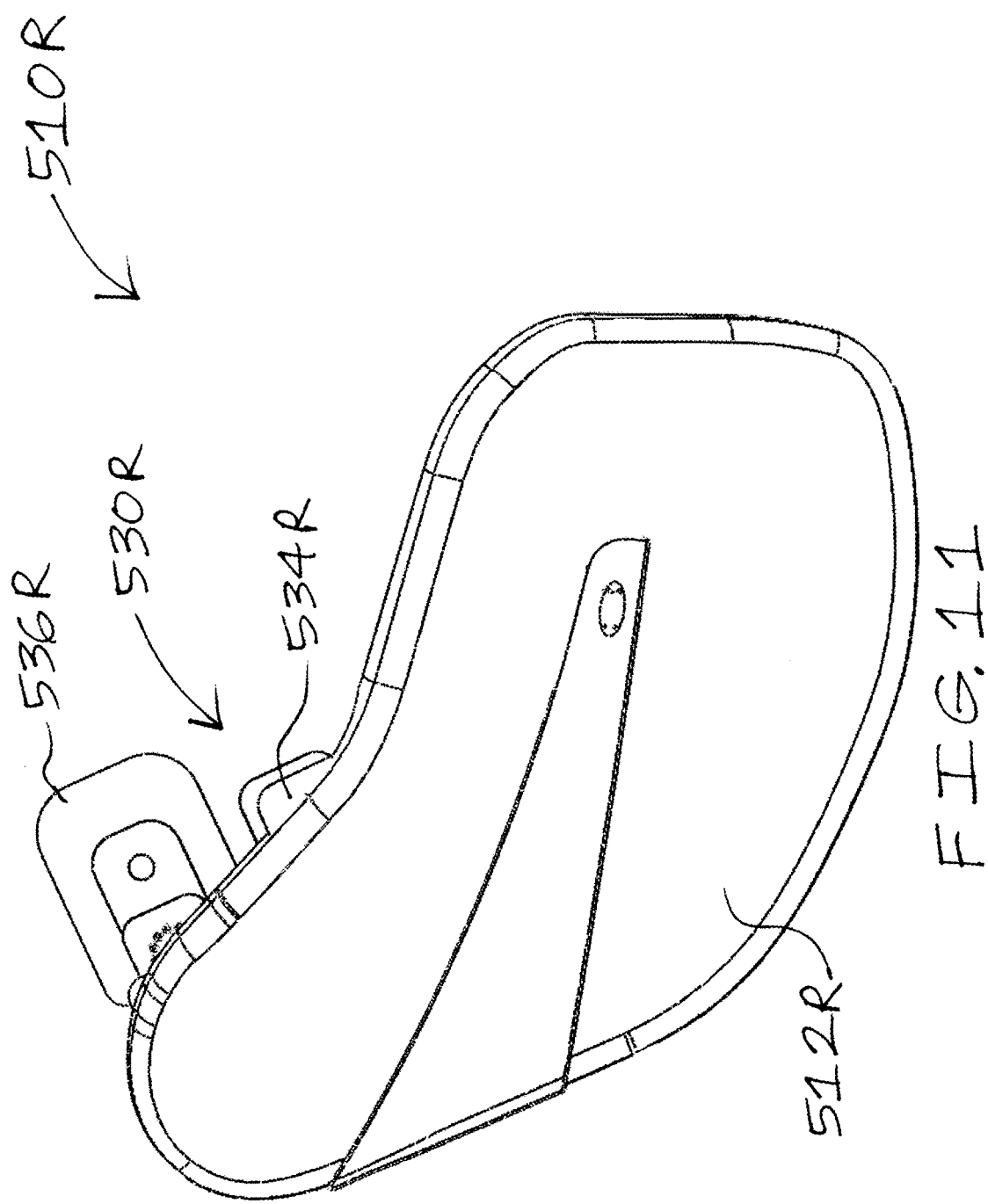

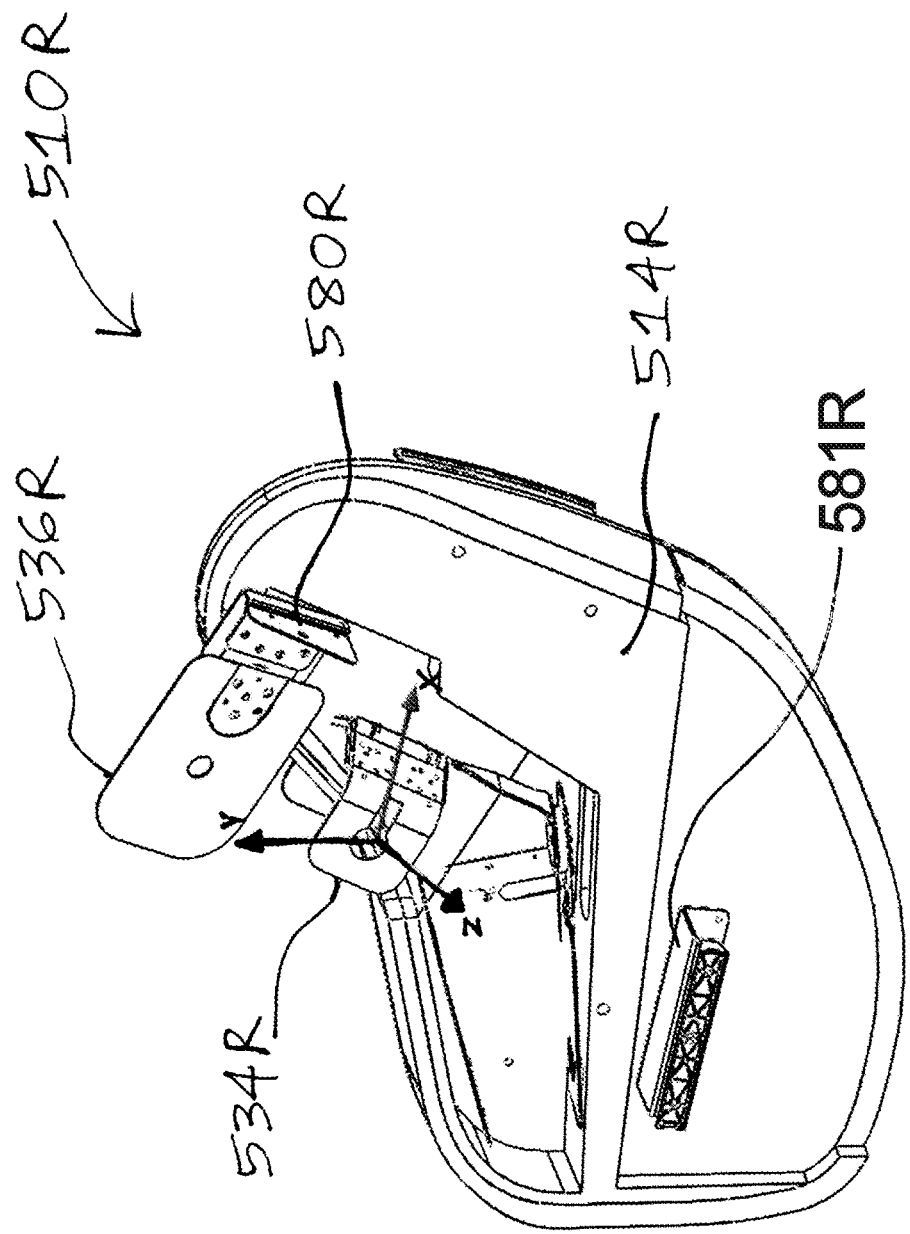

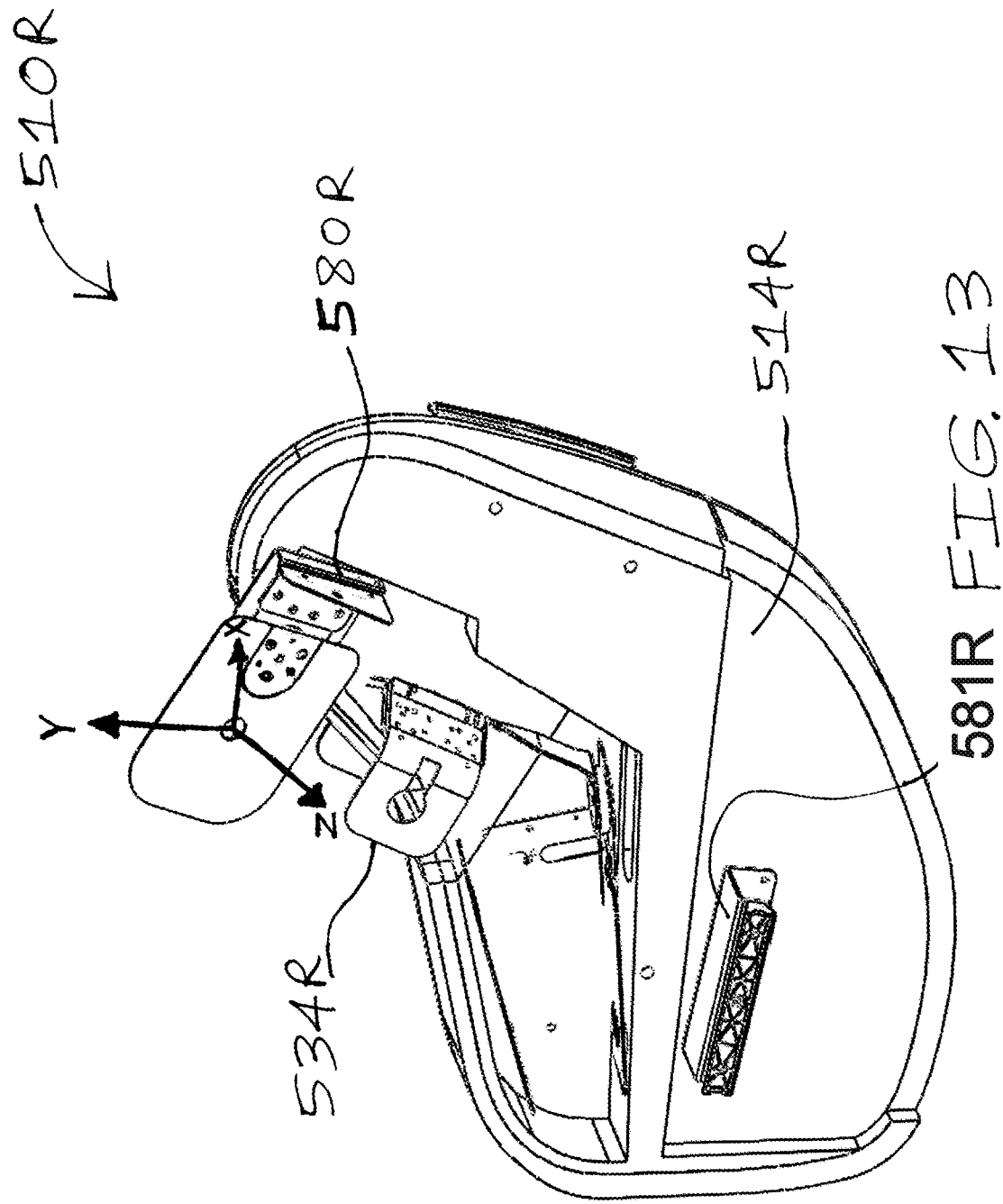

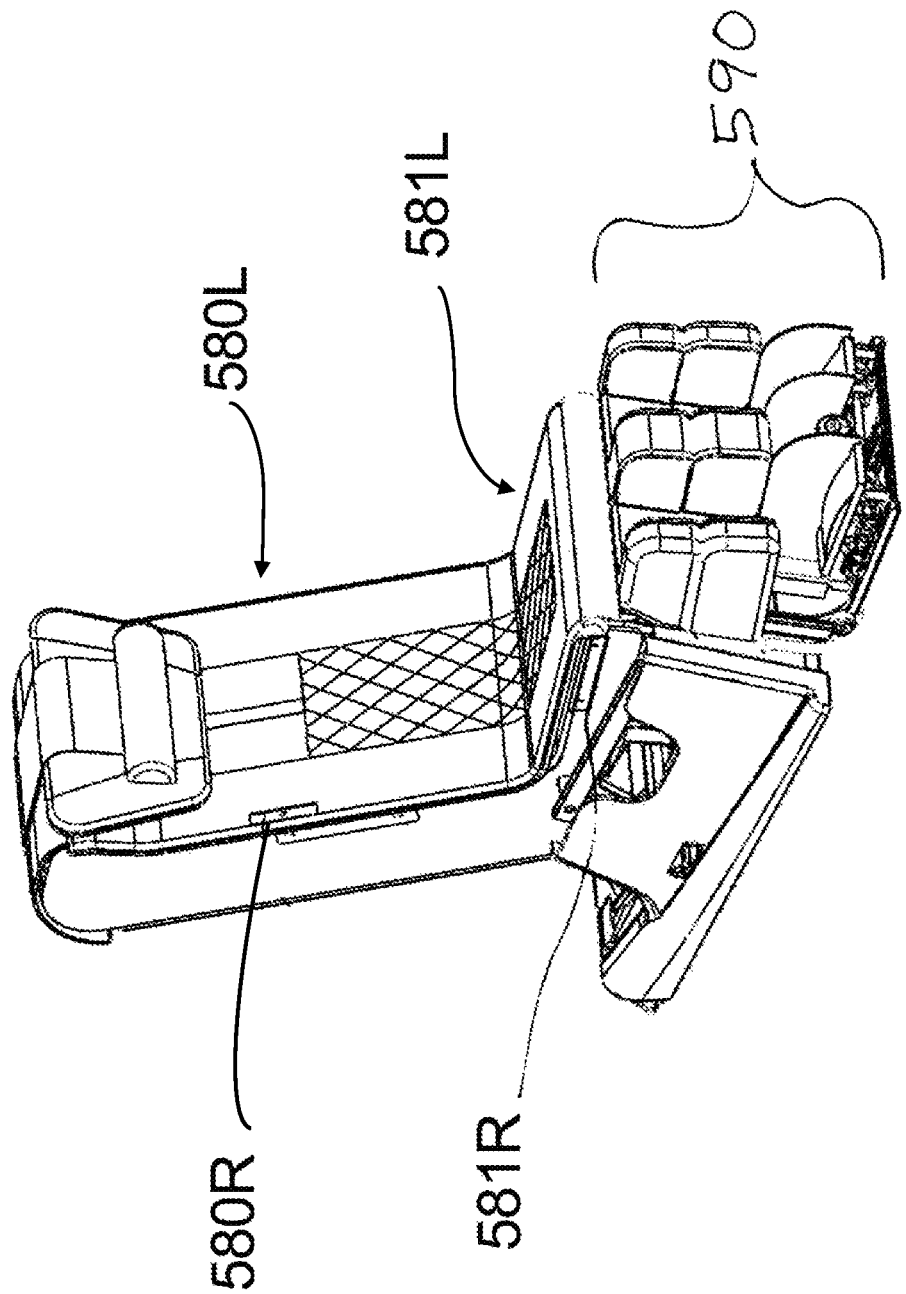

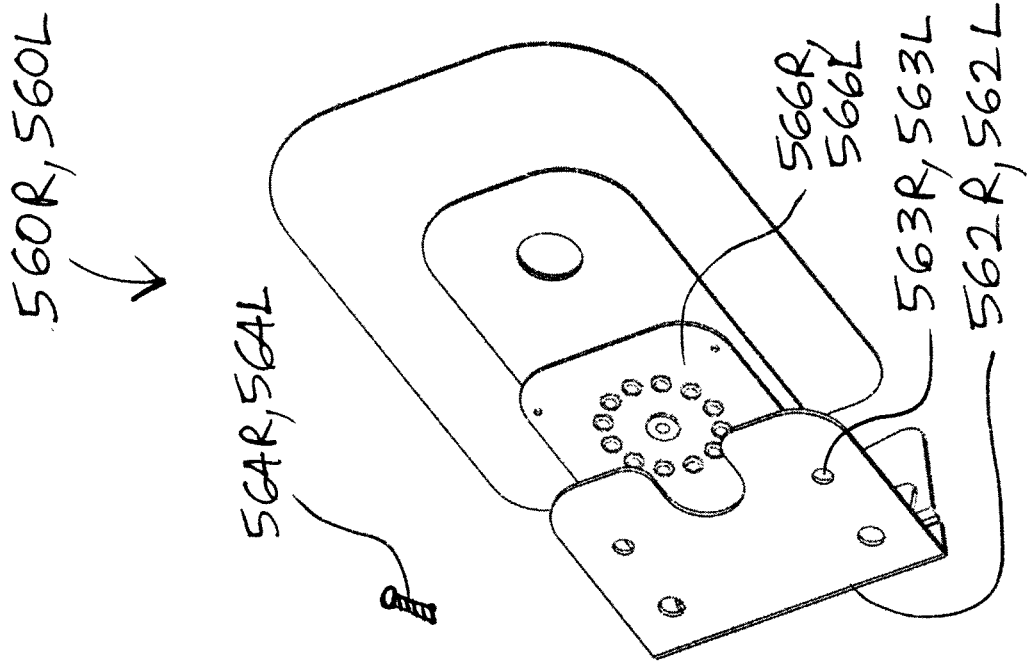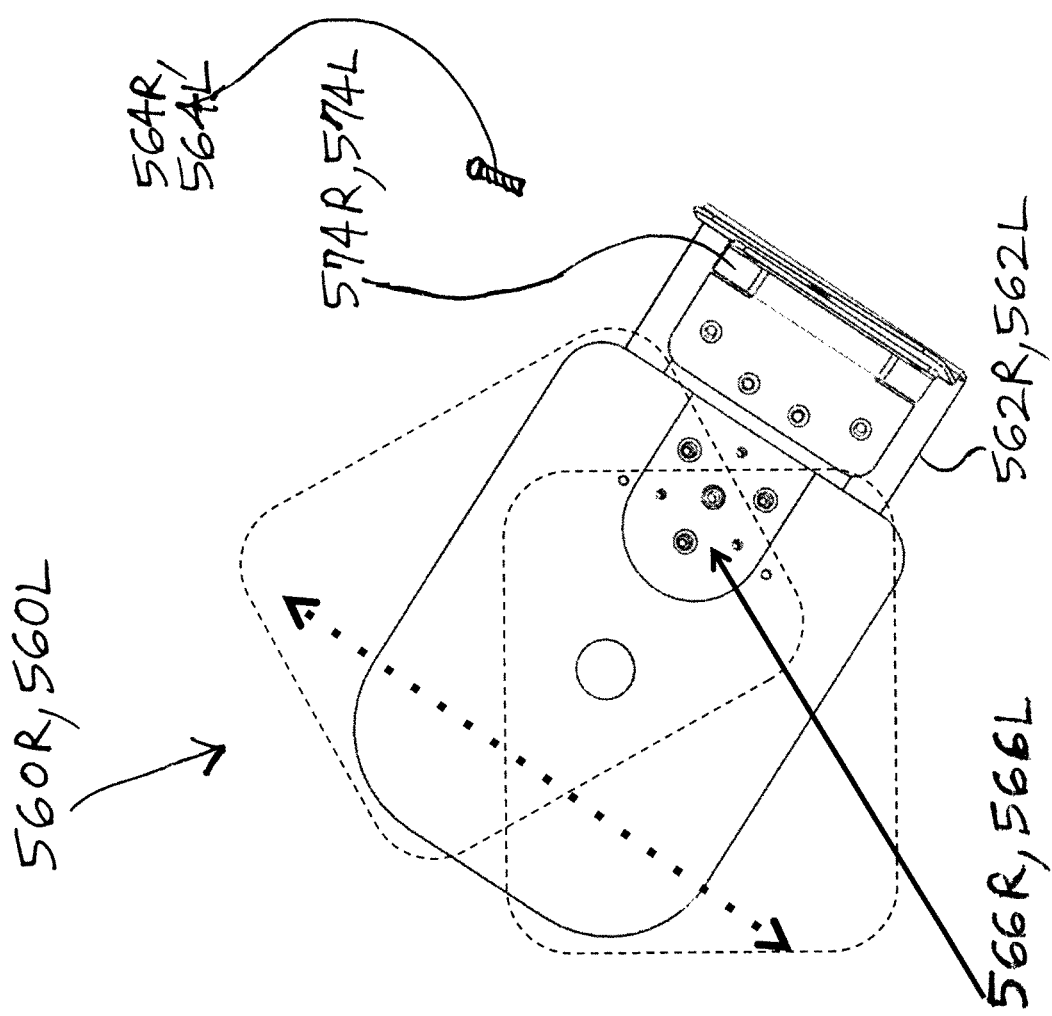

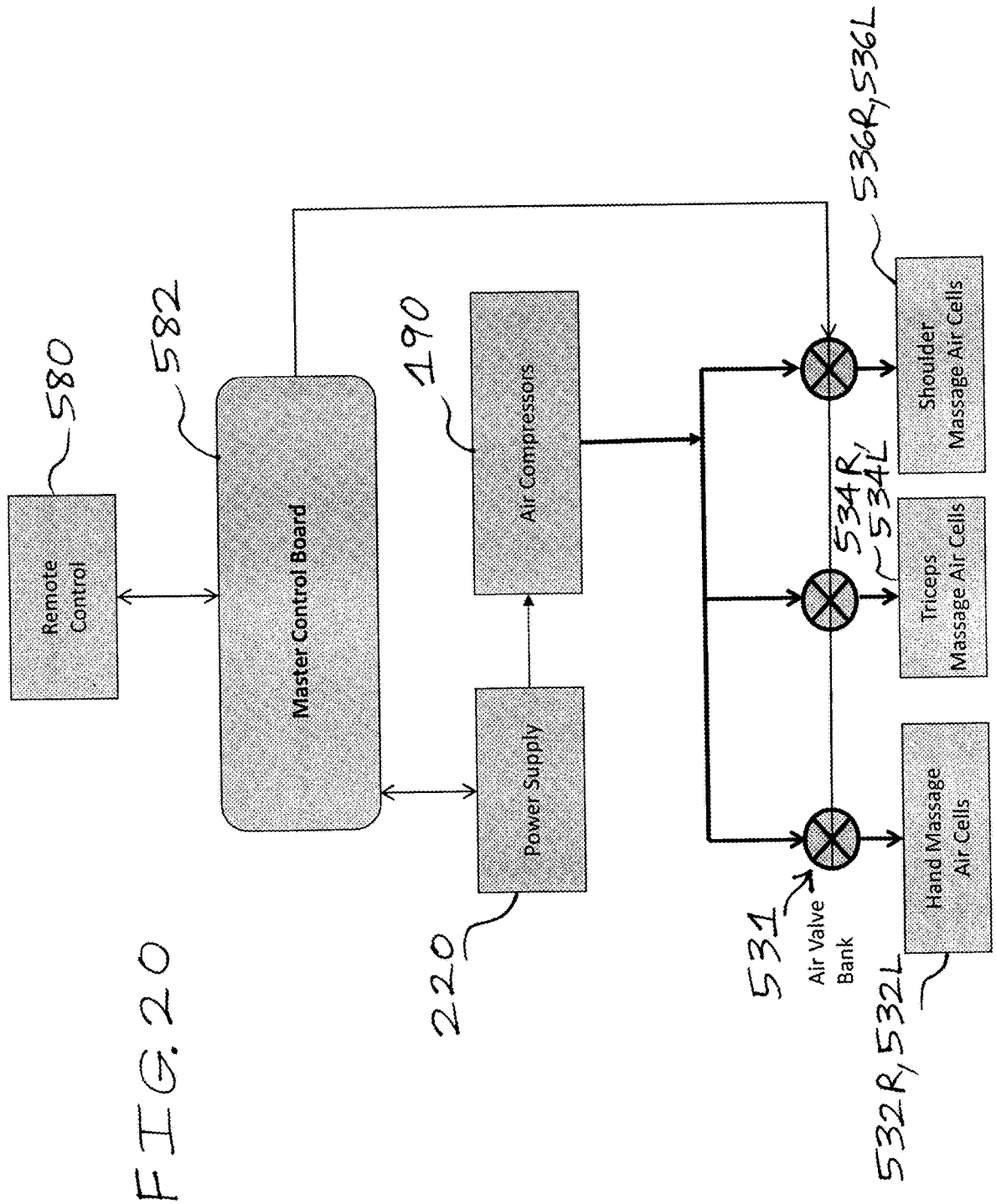

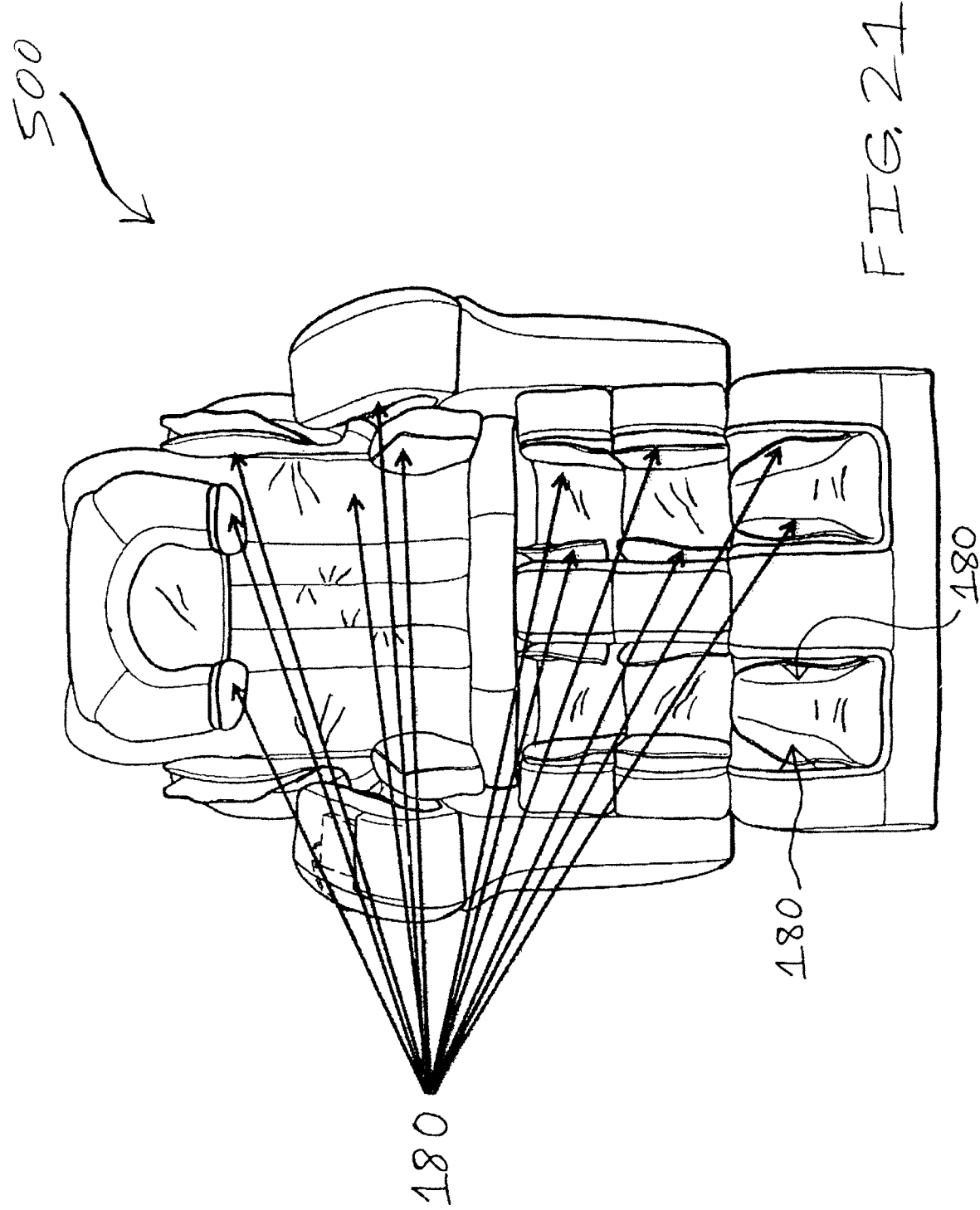

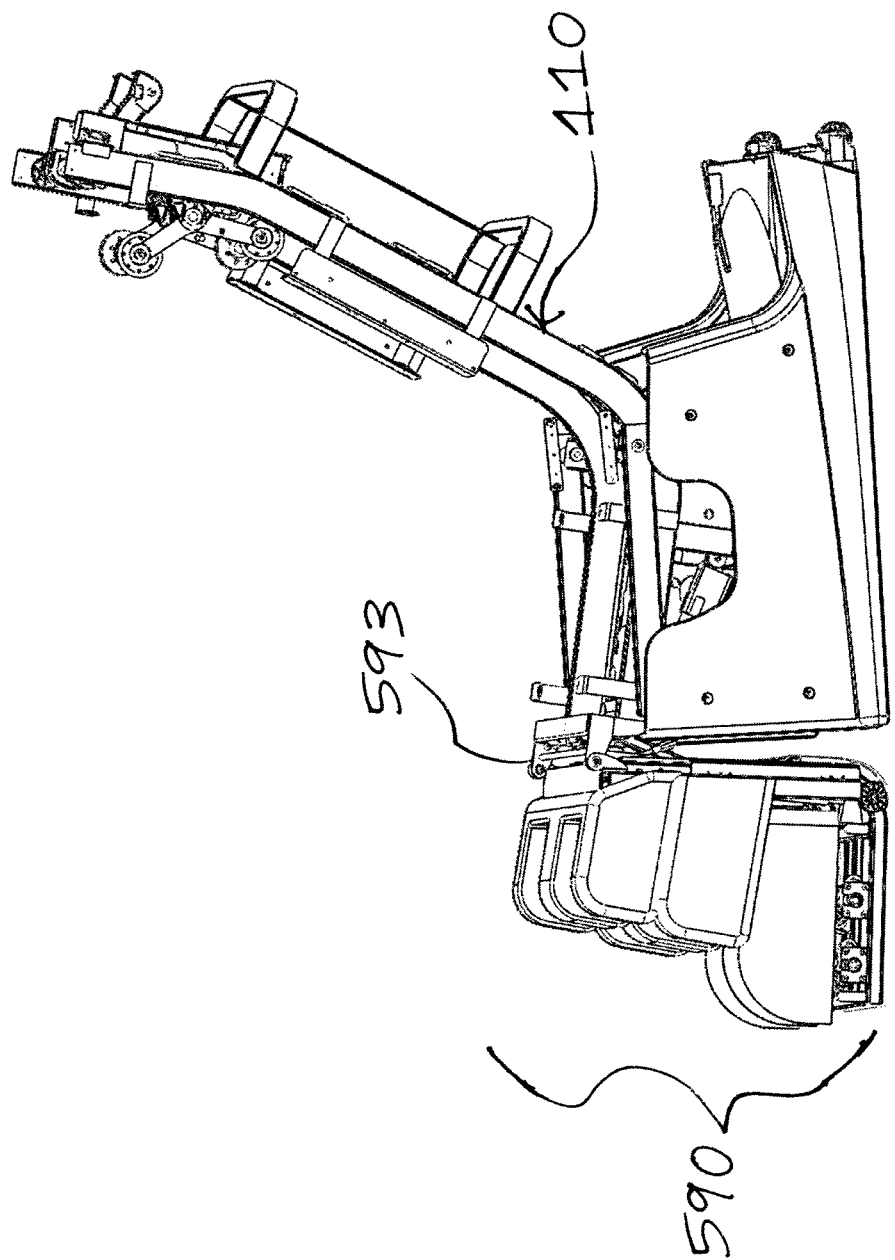

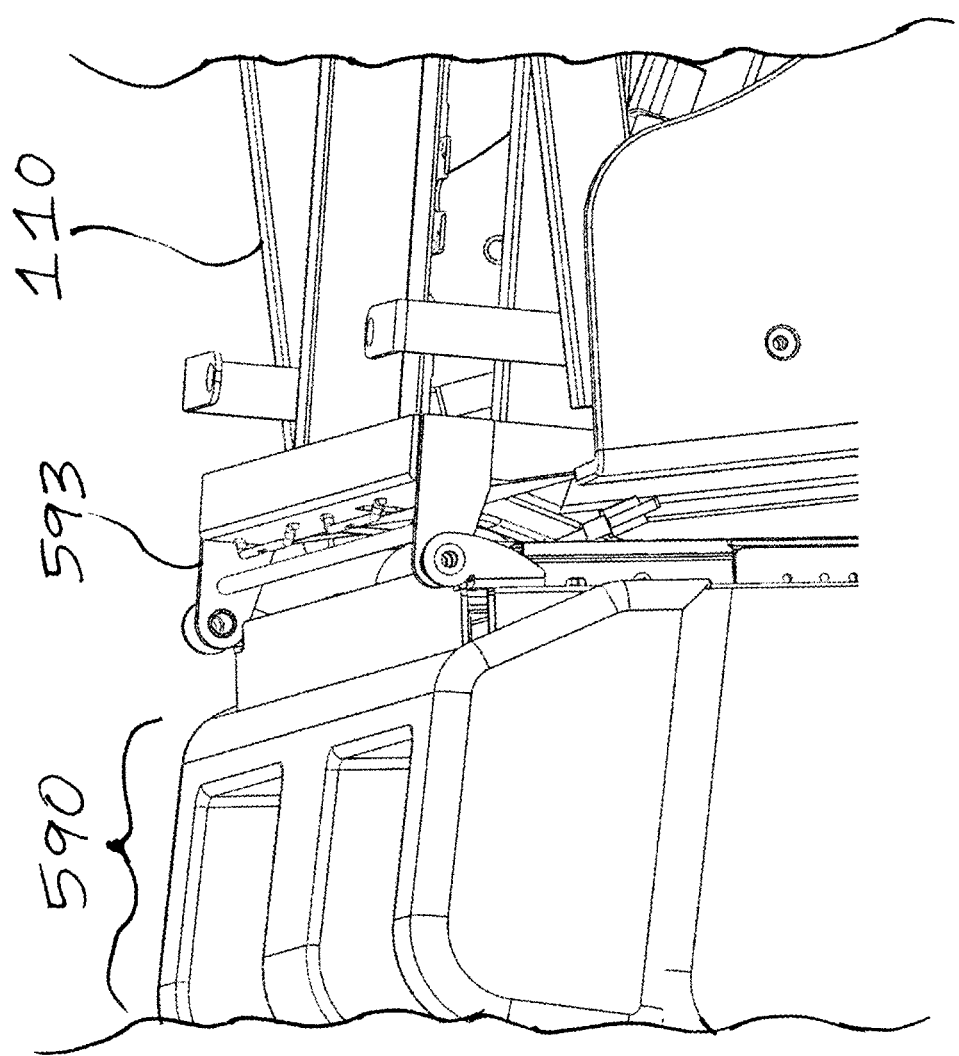

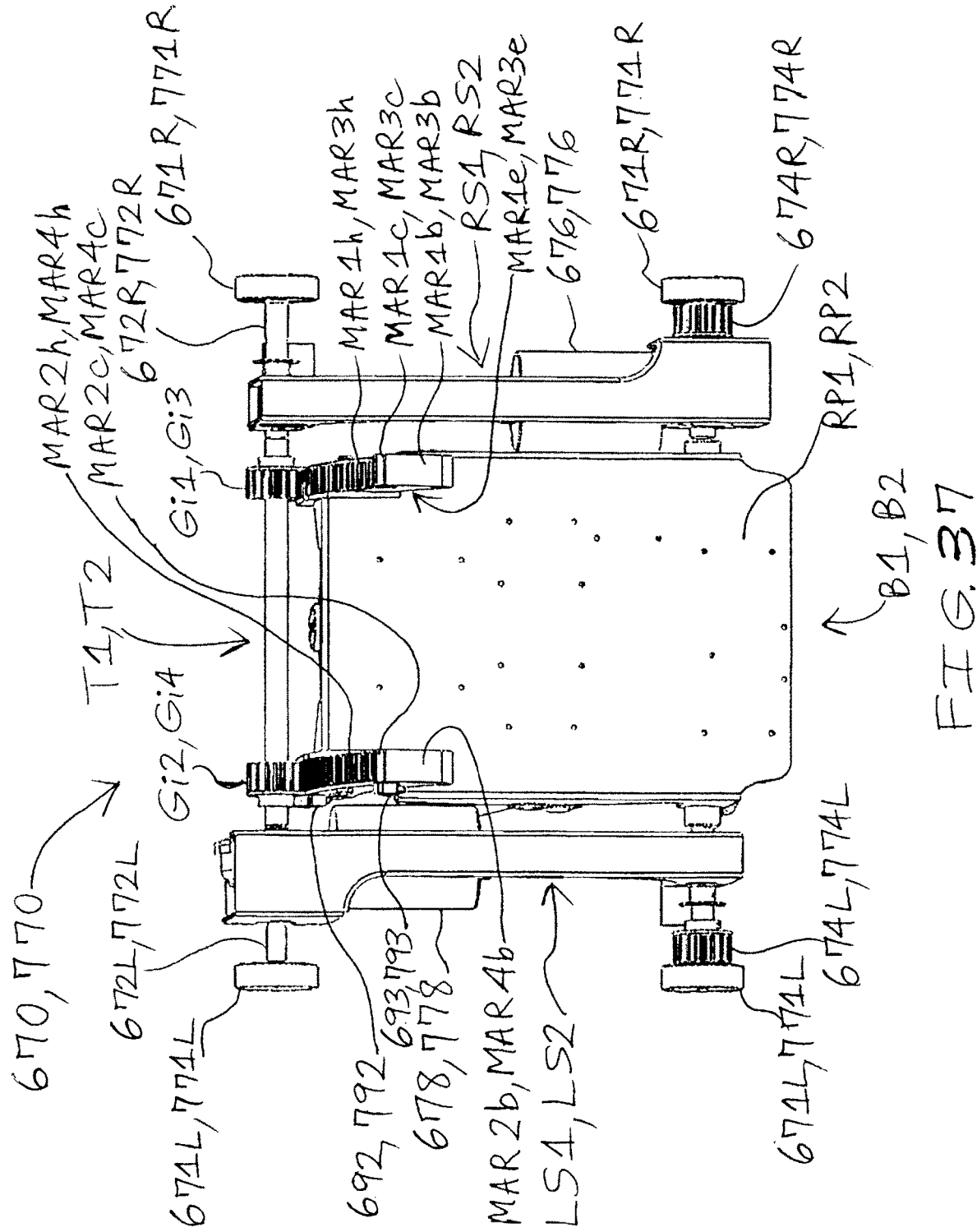

US 10,639,230 B2

MASSAGE CHAIR HAVING A MECHANISM FOR ADJUSTING POSITION OF FLUID MASSAGE ELEMENT FOR ARM MASSAGING

BACKGROUND OF THE INVENTION

Field of the Invention

The present invention generally relates to massage chairs and massage devices and apparatuses for massage chairs. More specifically, the present invention is directed to a massage chair having a mechanism for adjusting position of fluid massage element for arm massaging.

Description of the Related Art

Massage chairs and massage devices and apparatuses for massage chairs are known in the art.

There are many massage systems and devices of massage chairs that have a mechanism for adjusting massage element for body massaging and/or arm massaging. In some massage systems and devices related to massage chairs, the massage system or device may have an air compressor for pumping air into the air cells or bags throughout the massage chair to provide massage effects to users of the massage chair at air massage pressure points. Thus, a massage chair having a mechanism for adjusting position of massage element or fluid massage element for arm massaging is or may be desired.

The present invention overcomes one or more of the shortcomings of massage chairs and massage devices and apparatuses for massage chairs. The Applicant is unaware of inventions or patents, taken either singly or in combination, which are seen to describe the present invention as claimed.

SUMMARY OF THE INVENTION

The present invention is directed to a massage chair having a mechanism for adjusting position of fluid massage element for arm massaging.

As a first, non-limiting example, the massage chair preferably includes a massage chair frame; at least one arm massager apparatus (such as, but not limited to, at least one or a pair of arm panels or arm and shoulder panels wherein each or at least one panel has an arm massage system) positioned about (preferably secured to or about) a corresponding side of the massage chair frame; and a mechanism for securing the at least one arm massager apparatus to or about a corresponding side of the massage chair frame. In this example, the arm massage system comprises at least one fluid massage element for hand massaging, at least one fluid massage element for tricep massaging, at least one fluid massage element for shoulder massaging, a mechanism for adjusting position of the at least one fluid massage element for tricep massaging, and a mechanism for adjusting position of the at least one fluid massage element for shoulder massaging, respectively. The massage chair may further include a body massage system; a legs and feet massage apparatus that includes a legs and feet frame and a legs and feet massage system; and a noise-reducing (or noise-absorbing, noise-containing or noise-cancelling), enclosure device.

In a second, non-limiting example, it is preferred that the arm massage system comprises at least one fluid massage element for hand massaging, at least one fluid massage element for tricep massaging, and a mechanism for adjusting position of the at least one fluid massage element for tricep massaging, while the other components of the massage chair are included and are substantially the same as in the first, non-limiting example.

In a third, non-limiting example, it is preferred that the arm massage system comprises at least one fluid massage element for hand massaging, at least one fluid massage element for shoulder massaging, and a mechanism for adjusting position of the at least one fluid massage element for shoulder massaging while the other components of the massage chair are included and are substantially the same as in the first, non-limiting example.

BRIEF DESCRIPTION OF THE DRAWINGS

FIG. 11 is a right side, perspective view of an arm massager apparatus of the massage chair of FIG. 1, showing an outer side of the arm massager apparatus wherein a mechanism for adjusting position of the at least one fluid massage element for tricep massaging is in one tricep massaging position and a mechanism for adjusting position of the at least one fluid massage element for shoulder massaging is in one shoulder massaging position;

FIG. 12 is a right side, perspective view of the arm massager apparatus of FIG. 11, showing an inner side of the arm massager apparatus wherein the mechanism for adjusting position of the at least one fluid massage element for tricep massaging is in one tricep massaging position and the mechanism for adjusting position of the at least one fluid massage element for shoulder massaging is in one shoulder massaging position, and wherein the mechanism for adjusting position of the at least one fluid massage element for tricep massaging is able to move the fluid massage element (when secured to the mechanism) for tricep massaging in different, alternative positions relative to the x, y, and/or z axes;

FIG. 13 is a right side, perspective view of the arm massager apparatus of FIG. 11, showing an inner side of the arm massager apparatus wherein the mechanism for adjusting position of the at least one fluid massage element for tricep massaging is in one tricep massaging position and the mechanism for adjusting position of the at least one fluid massage element for shoulder massaging is in one shoulder massaging position, and wherein the mechanism for adjusting position of the at least one fluid massage element for shoulder massaging is able to move the fluid massage element (when secured to the mechanism) for shoulder massaging in different, alternative positions relative to the x, y, and/or z axes;

FIG. 14 is a right side, perspective view of the massage chair of FIG. 1, showing an absence of both of the arm massager apparatuses, and showing a mechanism for securing the at least one arm massager apparatus to or about a corresponding side of the massage chair frame;

FIG. 17 is a front perspective view of a mechanism for adjusting position of the at least one fluid massage element for shoulder massaging of the massage chair of FIG. 1;

FIG. 18 is a rear perspective view of the mechanism for adjusting position of the at least one fluid massage element for shoulder massaging of FIG. 17;

FIG. 20 is a massage control flow chart for a plurality of fluid massage elements of the massage chair of FIG. 1;

FIG. 21 is an elevated, front view of a massage chair according to the present invention, showing multiple locations where fluid massage elements may be positioned, and wherein similar fluid massage elements are or may be positioned in FIGS. 1-3;

FIG. 22 is a perspective, left side view of a massage chair having a legs and feet massage apparatus secured to a body massage apparatus according to the present invention, wherein a chair covering material is partially revealed to show a substantial portion of the body massage apparatus, and wherein the chair covering material is partially removed to show a portion of the legs and feet massage apparatus;

FIG. 23 is a close-up perspective view of the legs and feet massage apparatus secured to the body massage apparatus of FIG. 28;

FIG. 37 is an elevated, rear view of the body massage device of FIG. 34.

Figure 1:
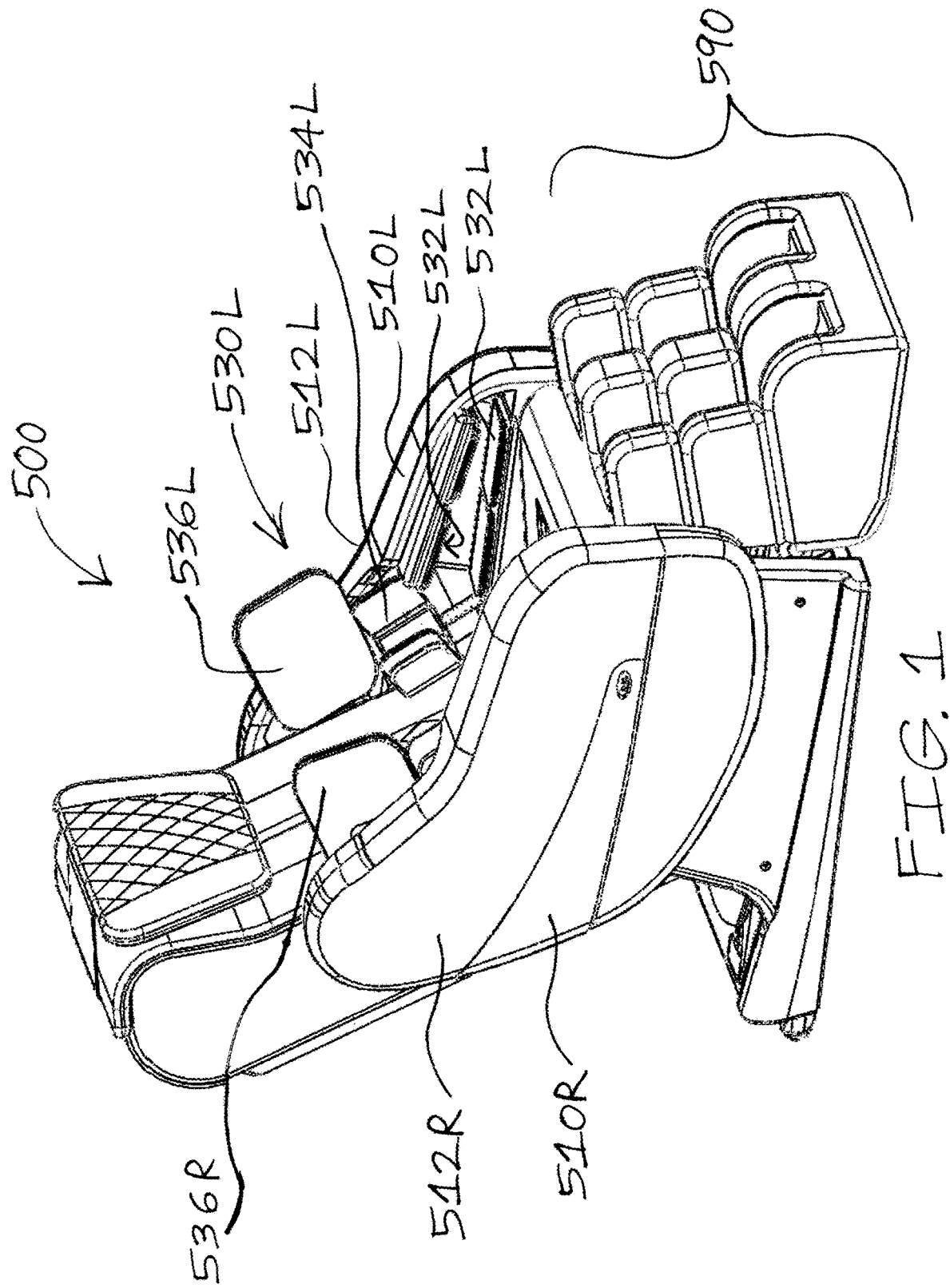
FIG. 1 is a right side, perspective view of a massage chair according to the present invention.

It should be understood that the above-attached figures are not intended to limit the scope of the present invention in any way.

DETAILED DESCRIPTION OF THE PREFERRED EMBODIMENTS

Referring to FIGS. 1-37, the present invention is directed to a massage chair 500 having a mechanism for adjusting position of fluid massage element for arm massaging.

As a first, non-limiting example of a first embodiment (shown in FIGS. 1-31), the massage chair 500 includes a massage chair frame 110; at least one arm massager apparatus 510R,510L (such as, but not limited to, at least one or a pair of arm panels or arm and shoulder panels 510R,510L wherein each or at least one panel 510R,510L has an arm massage system 530R,530L) positioned about (preferably secured to or about) a corresponding side 112R,112L of the massage chair frame 110; and a mechanism 580R,580L, 581R,581L for securing the at least one arm massager apparatus 510R,510L to or about a corresponding side 112R,112L of the massage chair frame 110. In this example, the arm massage system 530R,530L comprises at least one fluid massage element 532R,532L for hand massaging, at least one fluid massage element 534R,534L for tricep massaging, at least one fluid massage element 536R,536L for shoulder massaging, a mechanism 540R,540L for adjusting position of the at least one fluid massage element 534R,534L for tricep massaging, and a mechanism 560R,560L for adjusting position of the at least one fluid massage element 536R,536L for shoulder massaging, respectively. The massage chair 500 may further include a body massage system 170; a legs and feet massage apparatus 590 that includes a legs and feet frame 592 and a legs and feet massage system 594; and a noise-reducing (or noise-absorbing, noise-containing or noise-cancelling), enclosure device 230.

In a second, non-limiting example, it is preferred that the arm massage system 530R,530L comprises at least one fluid massage element 532R,532L for hand massaging, at least one fluid massage element 534R,534L for tricep massaging, and a mechanism 540R,540L for adjusting position of the at least one fluid massage element 534R,534L for tricep massaging, while the other components of the massage chair 500 are included and are substantially the same as in the first, non-limiting example.

In a third, non-limiting example, it is preferred that the arm massage system 530R,530L comprises at least one fluid massage element 532R,532L for hand massaging, at least one fluid massage element 536R,536L for shoulder massaging, and a mechanism 560R,560L for adjusting position of the at least one fluid massage element 536R,536L for shoulder massaging while the other components of the massage chair 500 are included and are substantially the same as in the first, non-limiting example.

The massage chair frame 110 includes a first end 122R, 122L, a second end 124R,124L, a right side 112R, a left side 112L, a seat or bottom body area portion 126R,126L, a back body area portion 128R,128L extending upward from the seat or bottom body area portion 126R,126L toward the second end 124R,124L, a thigh body area portion 125R, 125L located between the seat or bottom body area portion 126R,126L and the first end 122R,122L, and a head and neck body area portion 130R,130L extending upward from the back body area portion 128R,128L and located about the second end 124R,124L.

Figure 8:
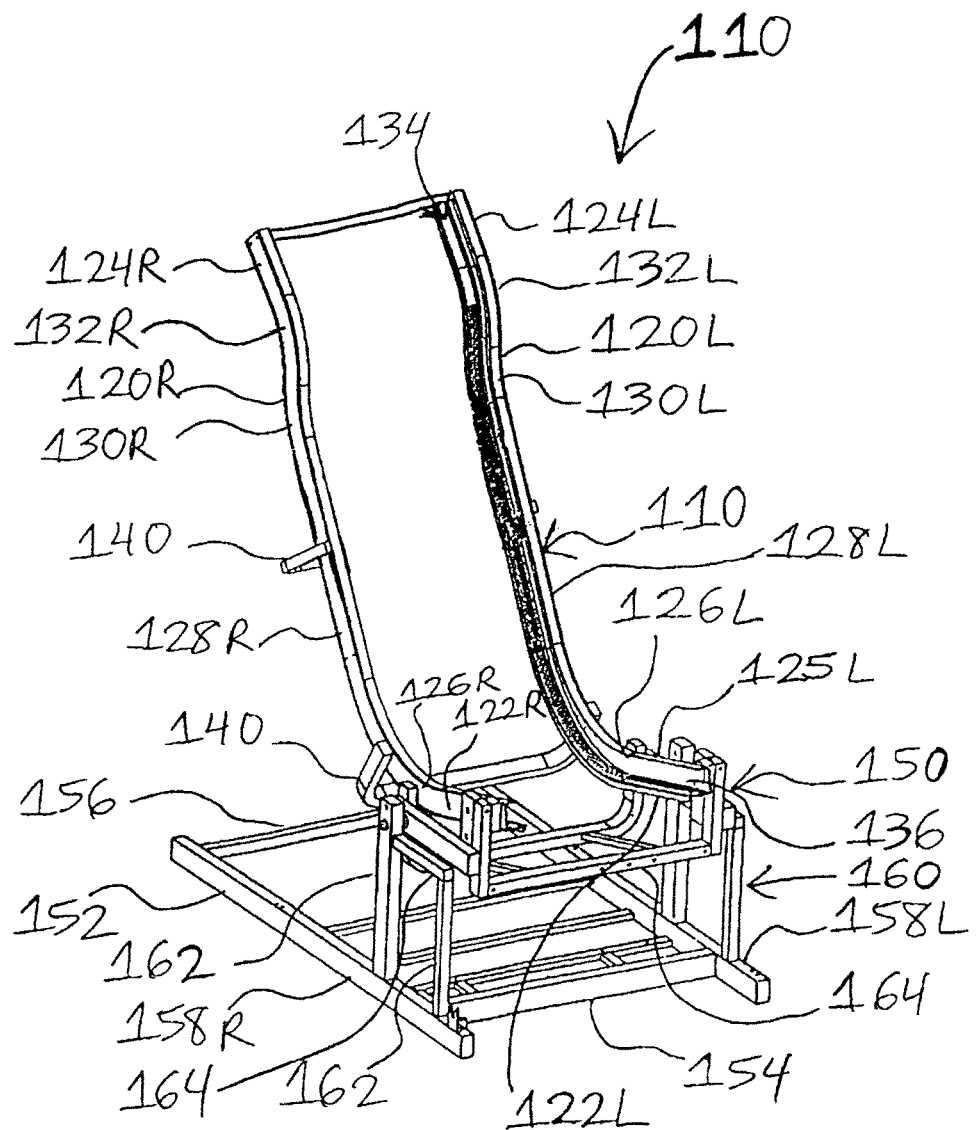
FIG. 8 is a front, right side perspective view of a massage chair frame of the massage chair of FIG. 1.
Figure 9:
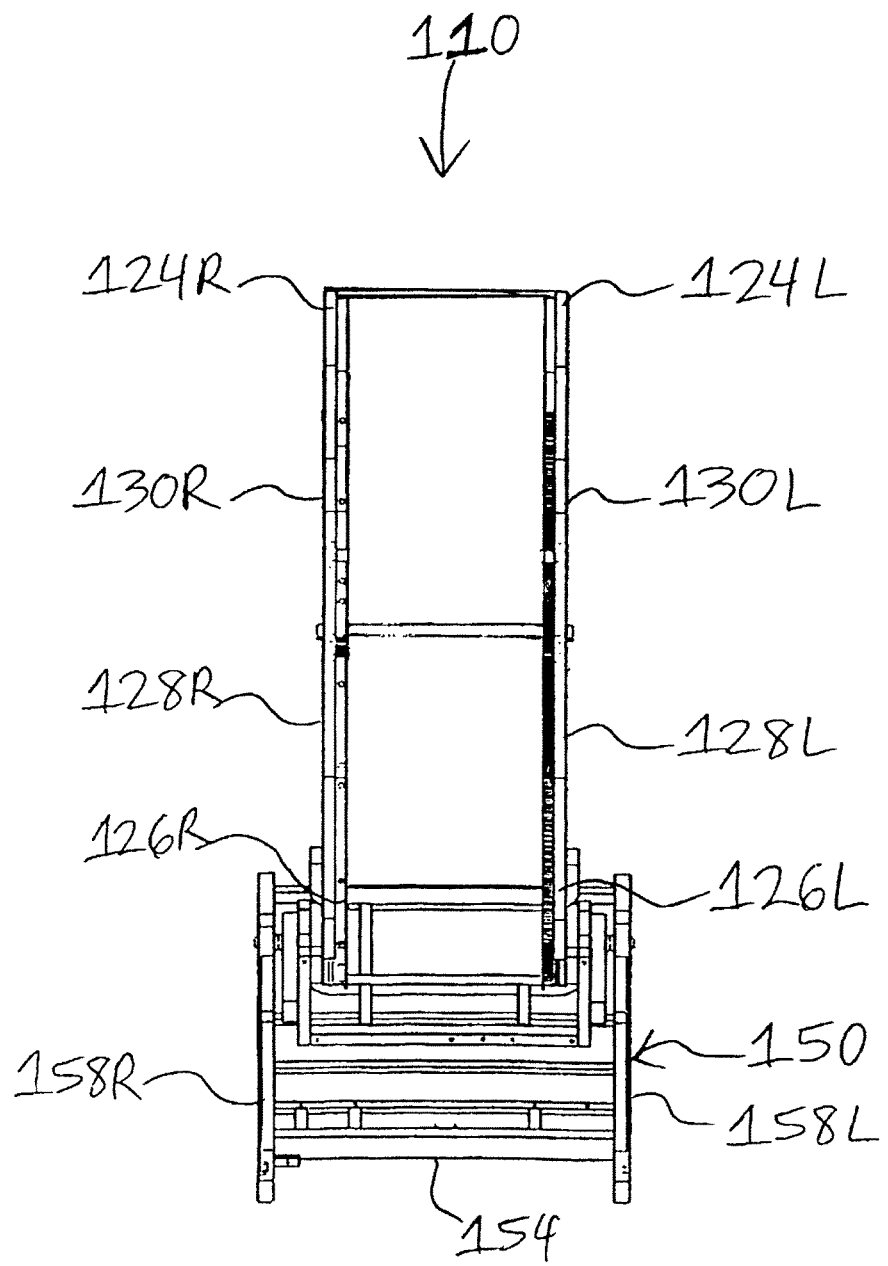
FIG. 9 is a rear view of the massage chair frame of FIG. 8.
Figure 10:
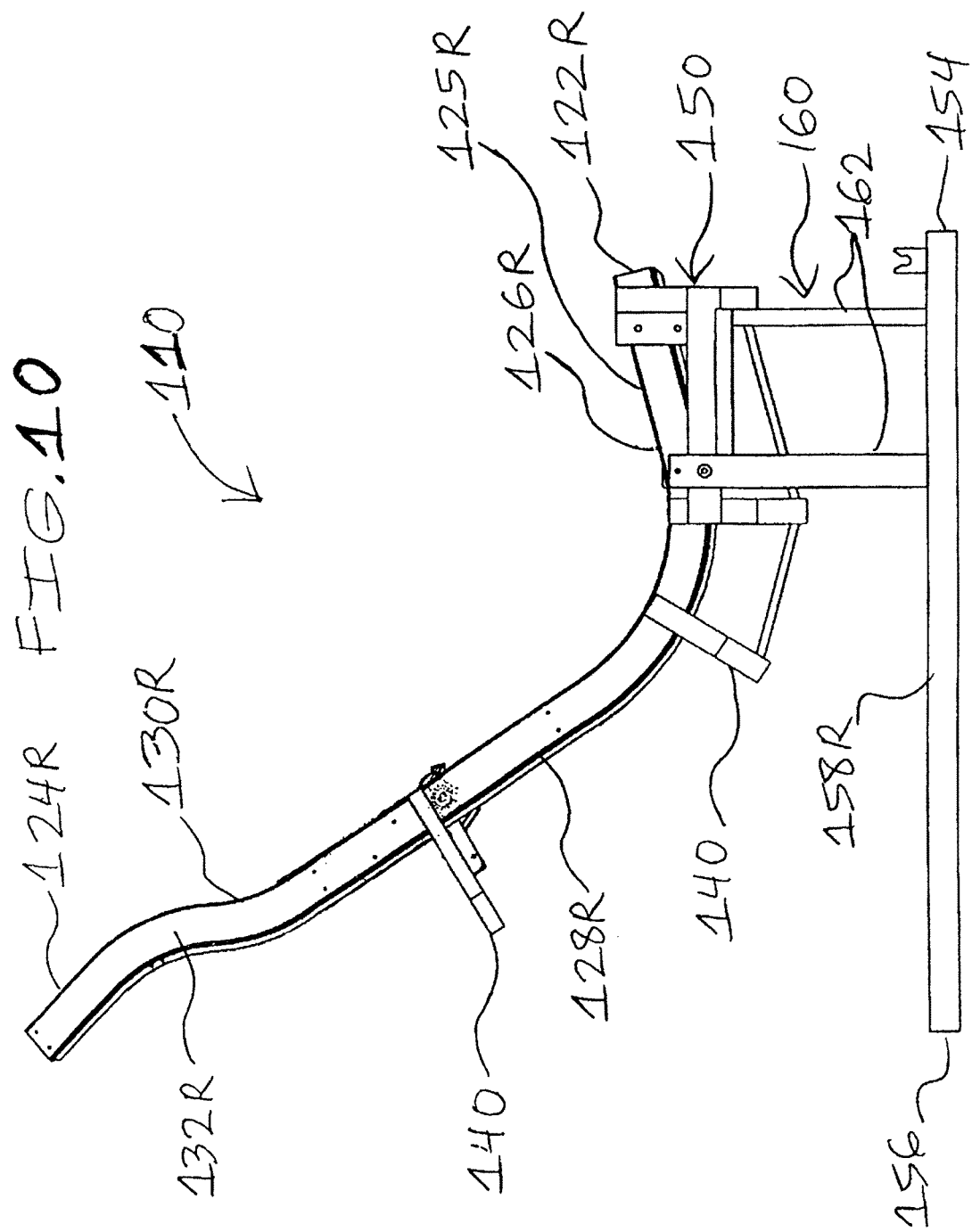
FIG. 10 is a right side view of the massage chair frame of FIG. 8.

As a non-limiting example and as best shown in FIGS. 8-10, the massage chair frame 110 includes a pair of opposing guide rails 120R,120L, a plurality of guide rails stabilizing bars 140, and a base stand 150. The guide rails 120R,120L are secured to the base stand 150, and are positioned generally above the base stand 150. The base stand 150 supports the weights of the guide rails 120R,120L and, preferably, also the weight of a user (not shown) of the massage chair 500.

Preferably, the guide rails 120R,120L are substantially similar or mirror images of one another. Each of the guide rails 120R,120L includes a first end 122R,122L, a second end 124R,124L, a thigh body area portion 125R,125L located adjacent the first end 122R,122L, a seat or bottom body area portion 126R,126L located adjacent the thigh body area portion 125R,125L and away from the first end 122R,122L, a back body area portion 128R,128L extending upward from the bottom body area portion 126R,126L, a head and neck body area portion 130R,130L extending upward from the back body area portion 128R,128L and located about the second end 124R,124L, an outer side 132R,132L, an inner side 134, and a guide channel 136 extending from the thigh body area portion 125R,125L to the back body area portion 128R,128L, preferably to the head and neck body area portion 130R,130L, and running along the inner side 134 of the guide rail 120R,120L. The guide channel 136 may include gear teeth 138 for engaging with at least one gear member from a mechanical massage device (not shown) when the mechanical massage device moves upward and downward in a generally vertical direction from the first end 122R,122L toward the second end 124R,124L of the guide rail 120R,120L and vice versa, respectively. Preferably, each of the guide rails 120R,120L has a generally "L-shaped" configuration. In this configuration, the lower portion of the "L" includes the thigh body area portion 125R,125L and bottom body area portion 126R,126L, and the upper portion of the "L" includes the back body area portion 128R,128L and head and neck body area portion 130R,130L. As best shown in 8-10, more preferably, each of the guide rails 120R,120L has a reclining "L-shaped" configuration.

The plurality of guide rails stabilizing bars 140 help to stabilize the positioning of the guide rails 120R,120L relative to one another. Each of the guide rails stabilizing bars 140 has a first end 142, a second end 144, and a body portion 146 extending from the first end 142 to the second end 144. Preferably, each of the guide rails stabilizing bars 140 has a generally "U-shaped" configuration. The guide rails stabilizing bars 140 are secured at predetermined locations along the outer sides 132R,132L of the guide rails 120R,120L.

The base stand 150 includes a base 152 and a guide rails support structure 160. The base 152 includes a first or front end 154, a second or rear end 156, and a pair of opposing sides 158R,158L. The guide rails support structure 160 is secured about the front end 154 of the base 152, and is positioned above the base 152. The guide rails support structure 160 includes a plurality of vertical bars or members 162 and a plurality of horizontal bars or members 164. The plurality of vertical bars 162 extend upward from the pair of opposing sides 158R,158L of the base 152, and, along with the plurality of horizontal bars 164, form a support frame with a "square-shaped" or "rectangular-shaped" box configuration.

Since the base stand 150 supports the weights of the guide rails 120R,120L and user of the massage chair 500, the base stand 150 is preferably made or manufactured of a strong material, such as, but not limited to, steel, metal, wood, hard plastic, any material or combination of materials known to one of ordinary skill in the art, and any combination thereof. Also, each of the guide rails 120R,120L and plurality of guide rails stabilizing bars 140 may be made or manufactured of steel, metal, wood, plastic, any material or combination of materials known to one of ordinary skill in the art, and any combination thereof.

As best shown in FIGS. 1-7 and 11-13, the at least one arm massager apparatus 510R,510L is preferably a right arm panel (or arm and shoulder panel) 510R and a left arm panel (or arm and shoulder panel) 510L that are secured to or about the right side 112R and left side 112L, respectively, of the massage chair frame 110. Preferably, each of the right arm panel 510R and left arm panel 510L has an outer side 512R,512L, an inner side 514R,514L, and an arm massage system 530R,530L.

The arm massage system 530R,530L comprises at least one fluid massage element 532R,532L for hand massaging, at least one fluid massage element 534R,534L for tricep massaging, at least one fluid massage element 536R,536L for shoulder massaging, a mechanism 540R,540L for adjusting position of the at least one fluid massage element 534R,534L for tricep massaging, and a mechanism 560R, 560L for adjusting position of the at least one fluid massage element 536R,536L for shoulder massaging, respectively.

Figure 2:
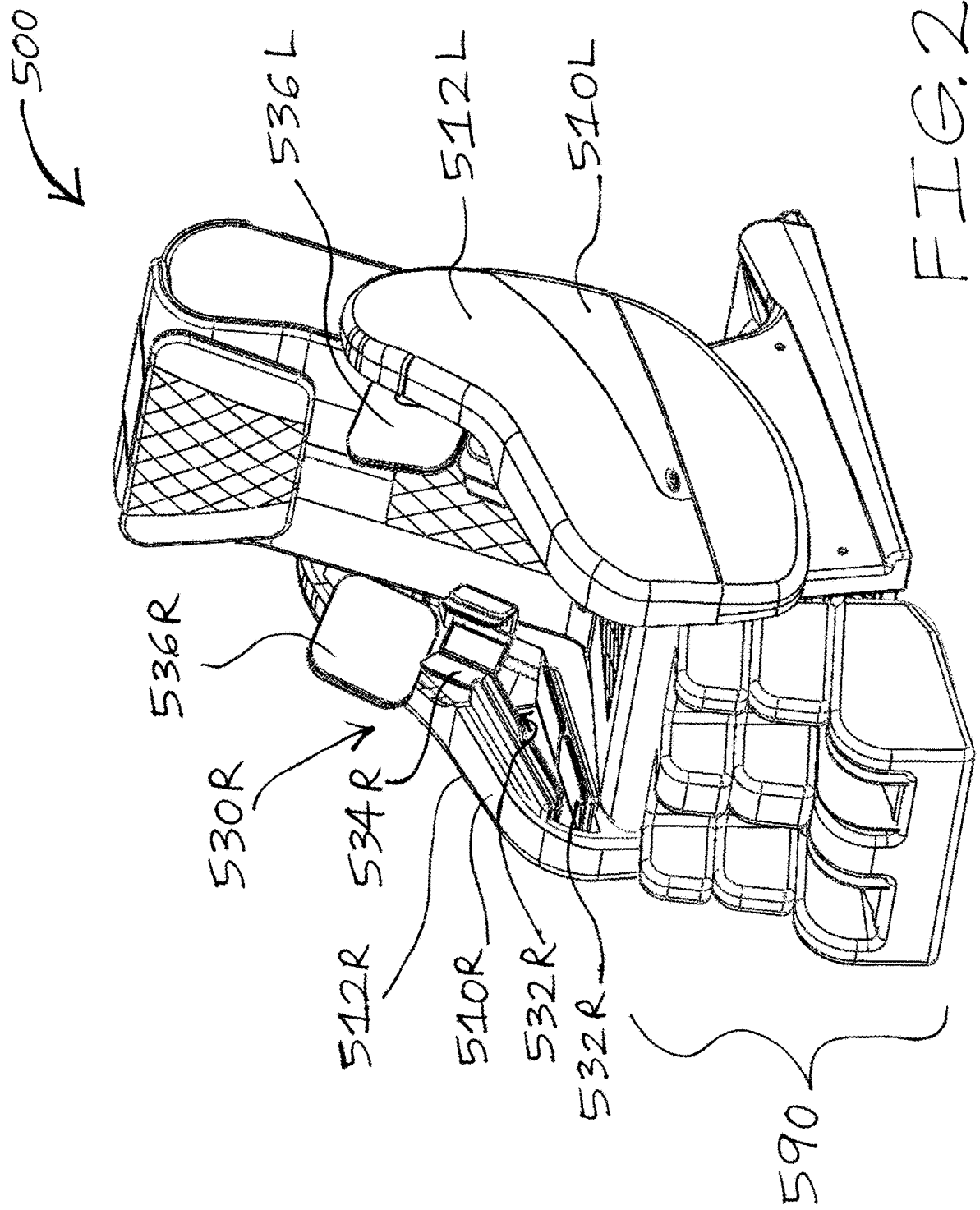
FIG. 2 is a left side, perspective view of the massage chair of FIG. 1.

Preferably, the at least one fluid massage element 532R, 532L for hand massaging is/are positioned at a predetermined hand massaging position(s) or at a starting or first hand massaging position(s) on or about the inner side 514R,514L of the arm panels 510R,510L, respectively, as shown in FIGS. 1 and 2, such that, during use or operation, the at least one fluid massage element 532R,532L for hand massaging provides massaging effects to a corresponding hand of the user.

Figure 3:
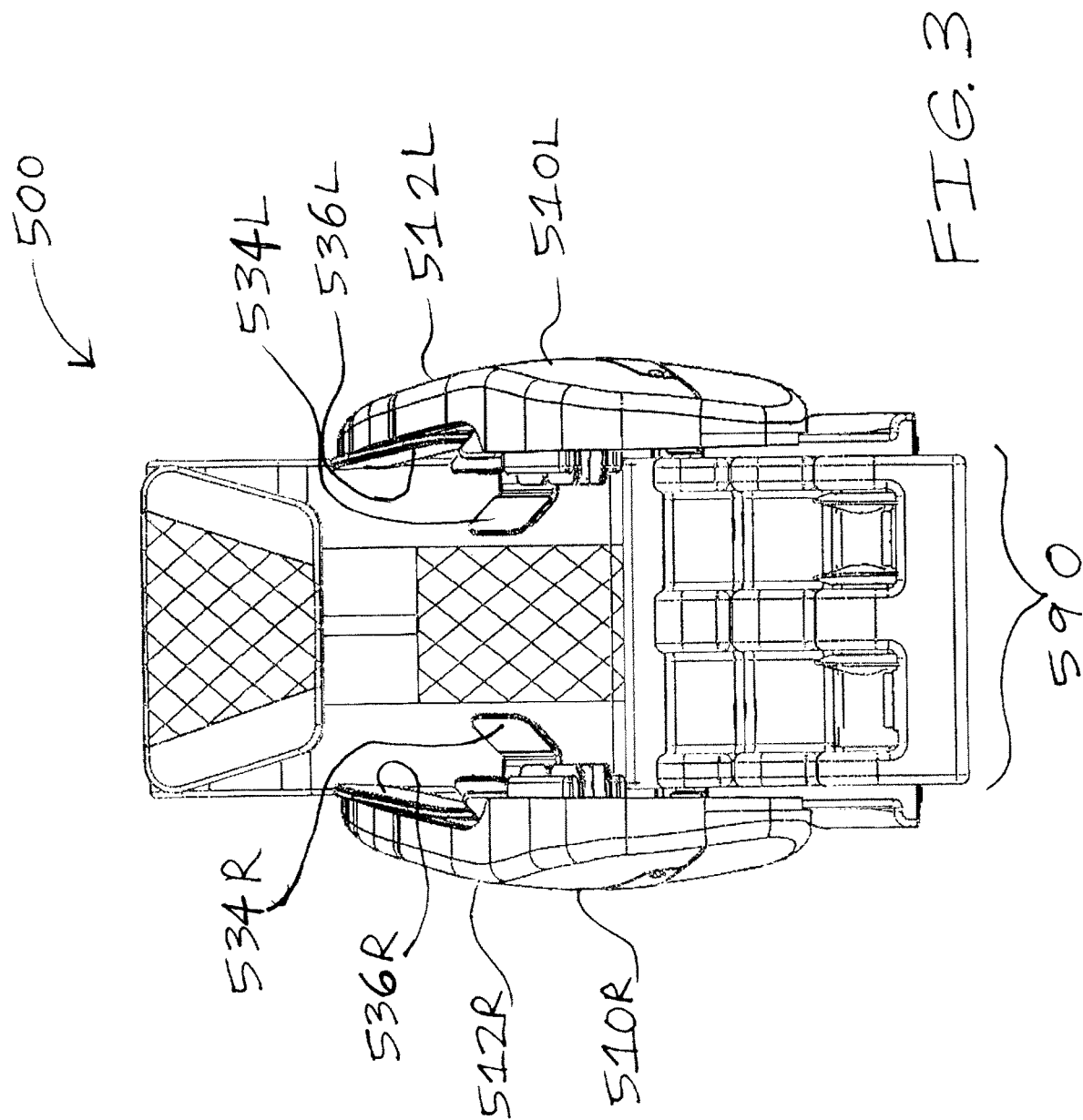
FIG. 3 is a front view of the massage chair of FIG. 1.
Figure 4:
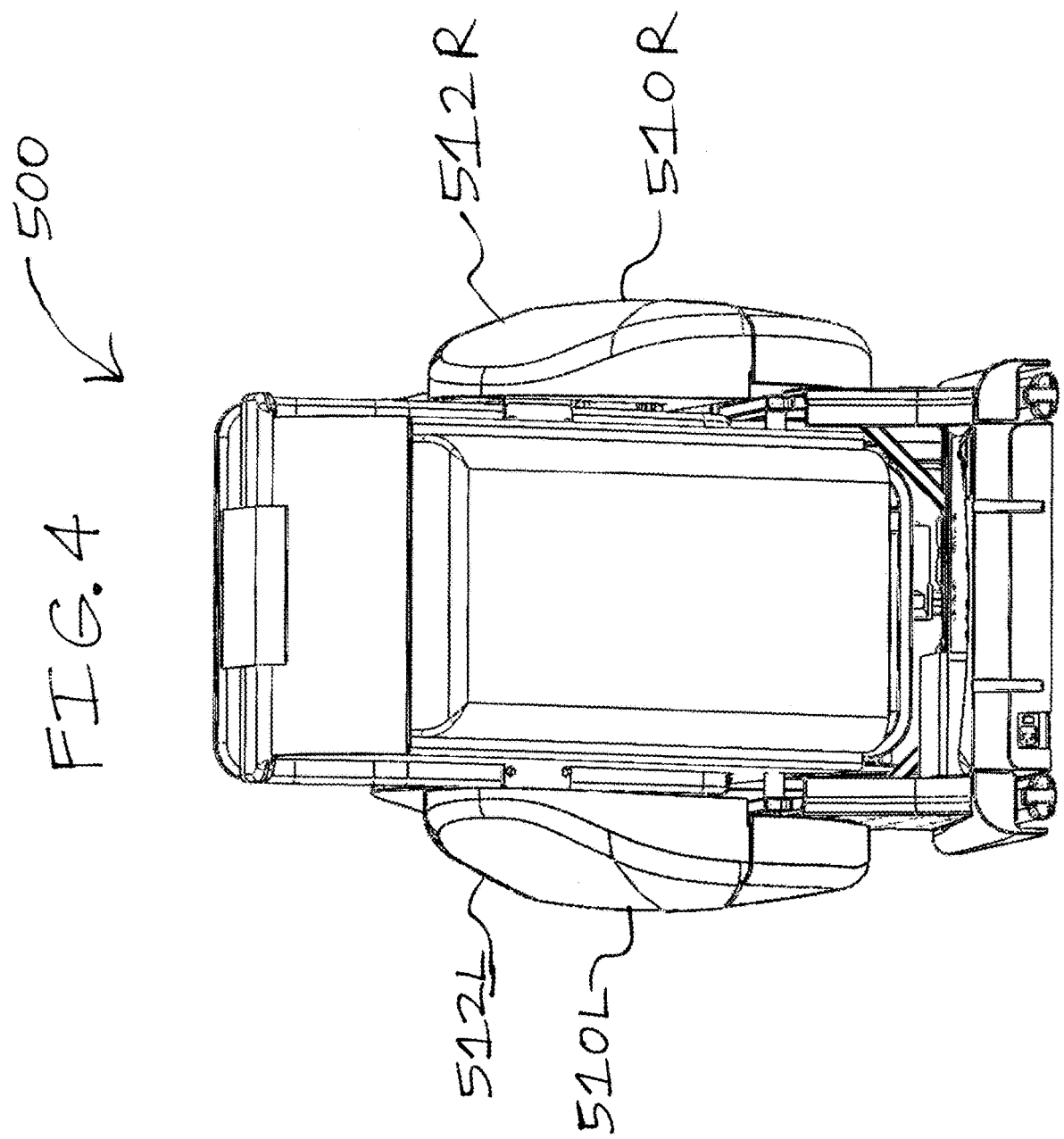
FIG. 4 is a rear view of the massage chair of FIG. 1.
Figure 5:
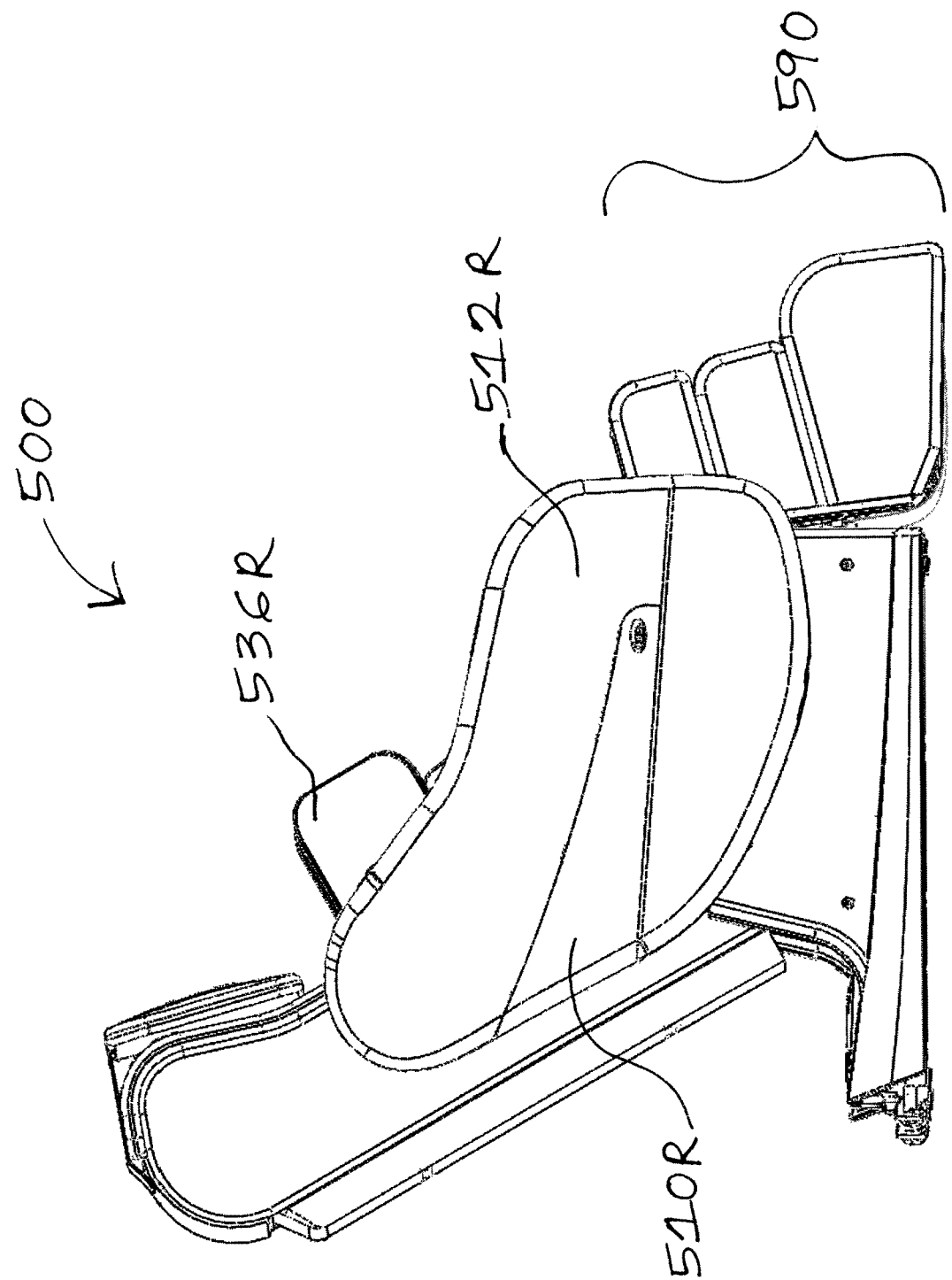
FIG. 5 is a right view of the massage chair of FIG. 1.
Figure 6:
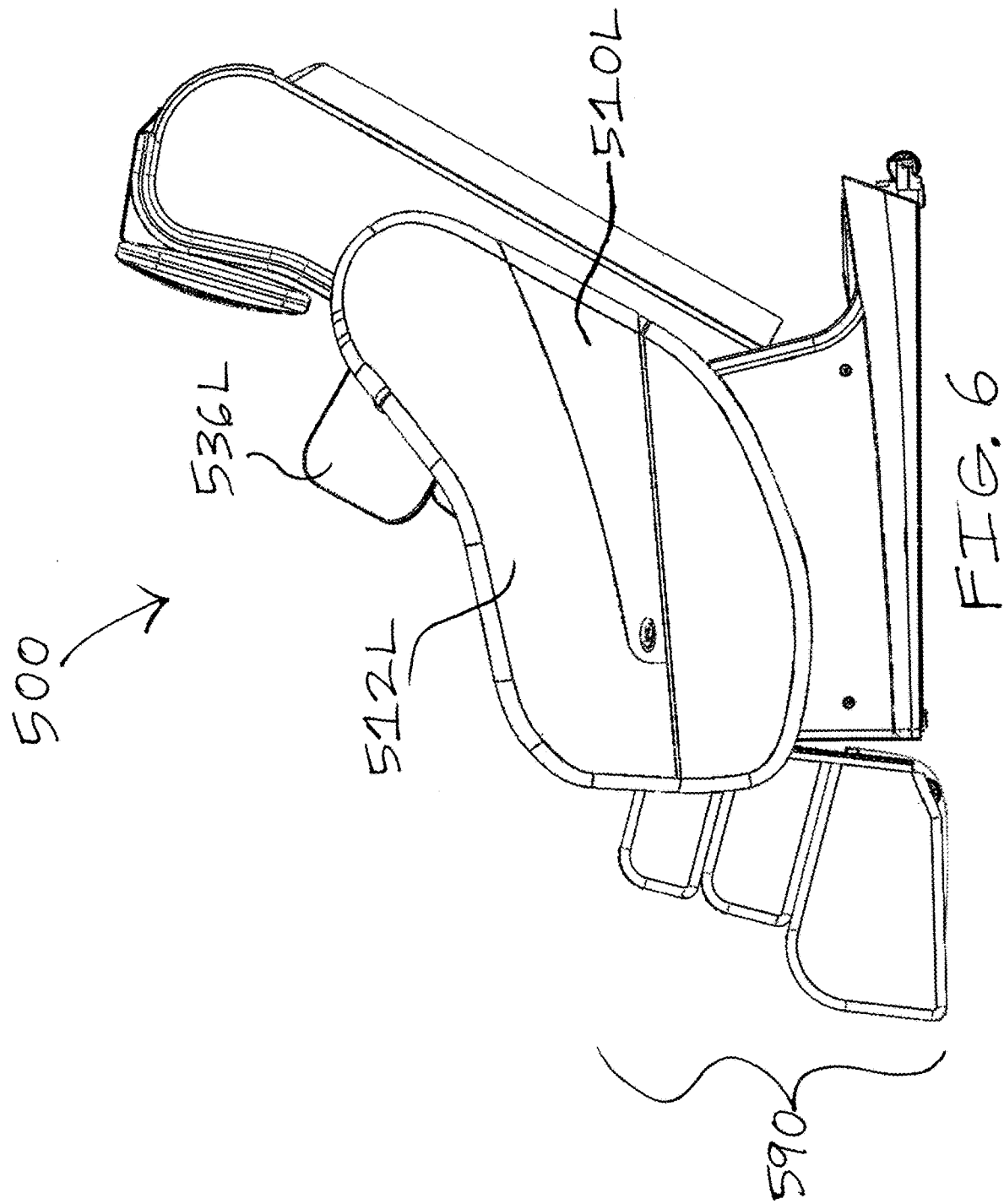
FIG. 6 is a left view of the massage chair of FIG. 1.
Figure 7:
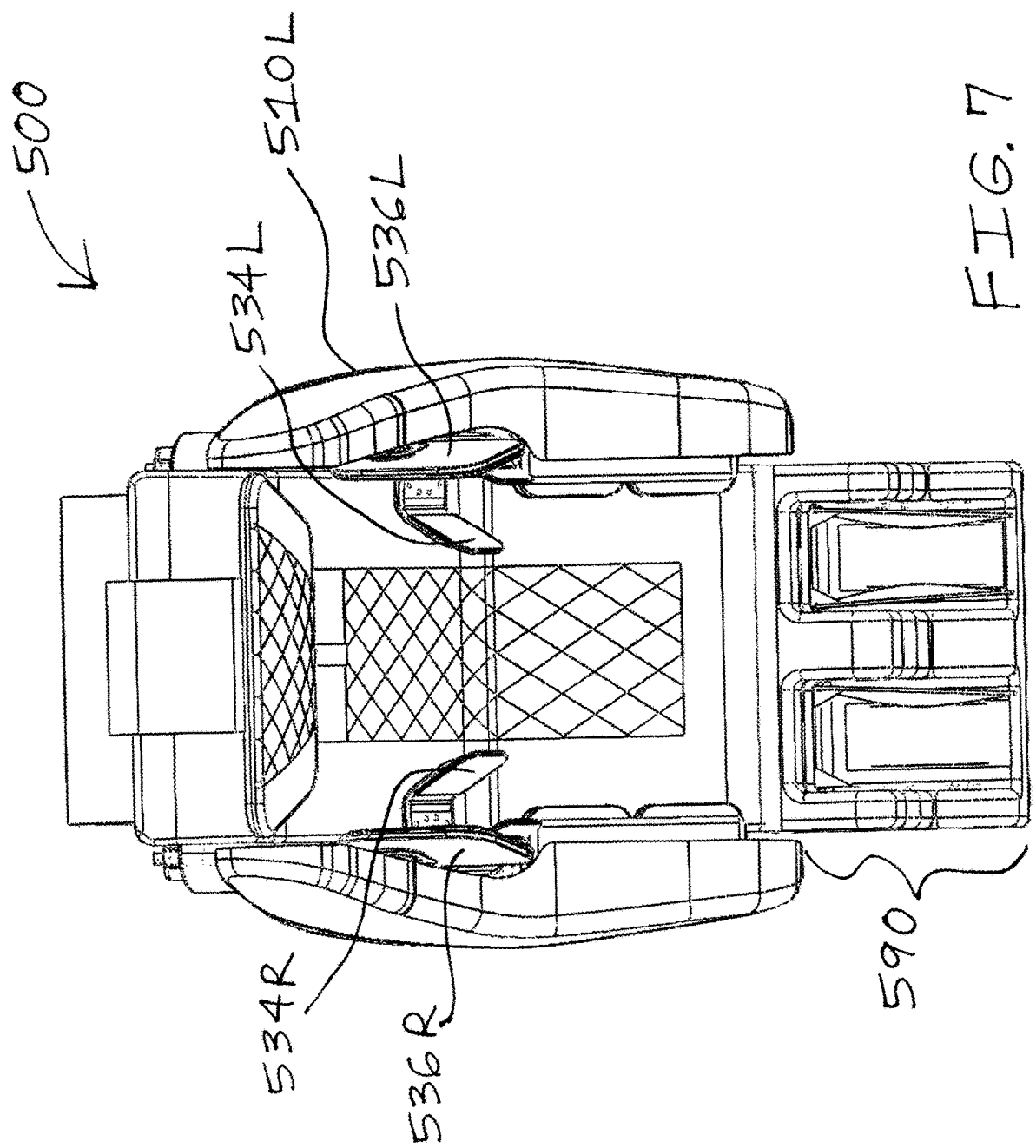
FIG. 7 is a top view of the massage chair of FIG. 1.

Preferably, the at least one fluid massage element 534R, 534L for tricep massaging is/are positioned, via the mechanism 540R,540L for adjusting position of the at least one fluid massage element 534R,534L for tricep massaging, at a predetermined tricep massaging position(s) or at a starting or first tricep massaging position(s) on or about the inner side 514R,514L of the arm panels 510R,510L, respectively, as shown in FIGS. 2, 3 and 7, such that, during use or operation, the at least one fluid massage element 534R,534L for tricep massaging provides massaging effects to a corresponding tricep of the user. Preferably, the at least one fluid massage element 534R,534L for tricep massaging is/are secured to the corresponding mechanism 540R,540L for adjusting position of the at least one fluid massage element 534R,534L for tricep massaging. Preferably, as best shown in FIGS. 11-13, the position of the at least one fluid massage element 534R,534L for tricep massaging can be adjusted, via the mechanism 540R,540L for adjusting position of the at least one fluid massage element 534R,534L for tricep massaging, such that massaging effects are able to be provided to corresponding triceps of a plurality of users who have different body sizes and different tricep sizes.

Preferably, the at least one fluid massage element 536R, 536L for shoulder massaging is/are positioned, via the mechanism 560R,560L for adjusting position of the at least one fluid massage element 536R,536L for shoulder massaging, at a predetermined shoulder massaging position(s) or at a starting or first shoulder massaging position(s) on or about the inner side 514R,514L of the arm panels 510R,510L, respectively, as shown in FIGS. 1-3 and 5-7, such that, during use or operation, the at least one fluid massage element 536R,536L for shoulder massaging provides massaging effects to a corresponding shoulder of the user. Preferably, the at least one fluid massage element 536R, 536L for shoulder massaging is/are secured to the corresponding mechanism 560R,560L for adjusting position of the at least one fluid massage element 536R,536L for shoulder massaging. Preferably, as shown in FIGS. 11-13, the position of the at least one fluid massage element 536R,536L for shoulder massaging can be adjusted, via the mechanism 560R,560L for adjusting position of the at least one fluid massage element 536R,536L for shoulder massaging, such that massaging effects are able to be provided to corresponding shoulders of a plurality of users who have different body sizes and different shoulder sizes.

Each of the plurality of fluid massage elements 532R, 532L,534R,534L, 536R,536L is adapted for having fluid transported or pumped into it by a fluid compressor or pump 190 and for having fluid withdrawn from it. The plurality of fluid massage elements 532R,532L,534R,534L,536R,536L may be a plurality of fluid massage cells or fluid massage bags (such as, but not limited to, air cell or air bags 180 shown in FIGS. 19A and 19B), any fluid massage element(s) known to one of ordinary skill in the art, and any combination thereof. The air cell 180 comprises an inflatable or expandable air cell housing 182, an air cell chamber 184 defined by the air cell housing 182, and an air cell inlet and outlet 186. The fluid that is contained in and/or pumped into and out of the plurality of fluid massage elements 180 may be air, a liquid, a gel, any fluid(s) known to one of ordinary skill in the art, and any combination thereof.

Figure 16:
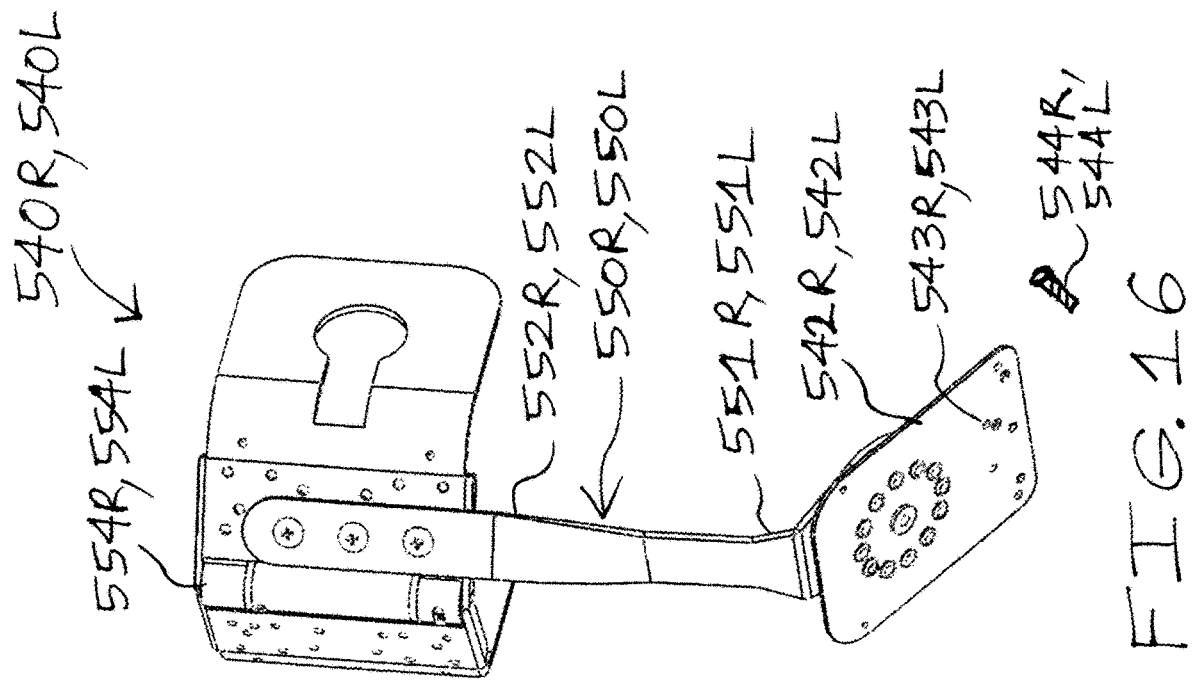
FIG. 16 is a rear perspective view of the mechanism for adjusting position of the at least one fluid massage element for tricep massaging of FIG. 15.
Figure 15:
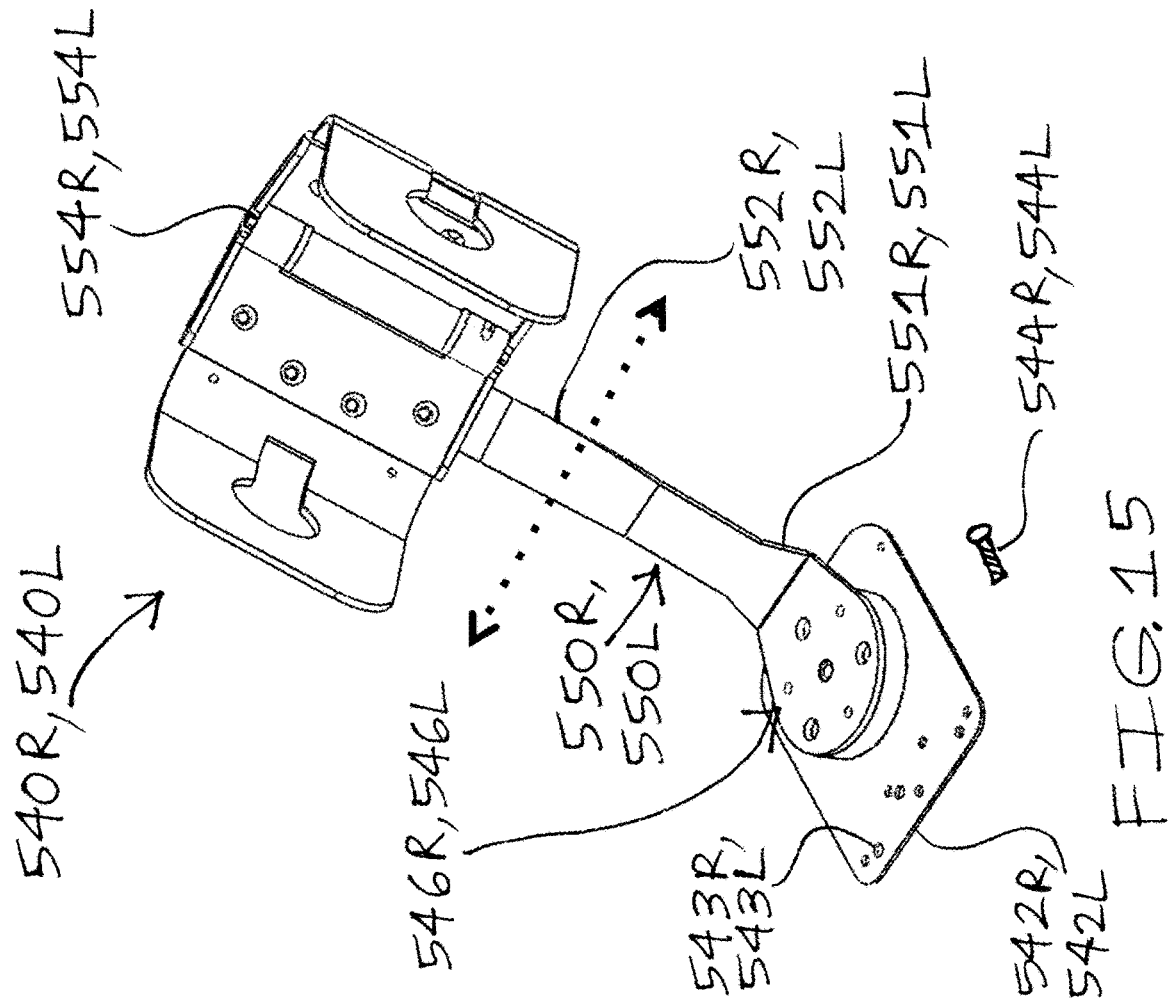
FIG. 15 is a front perspective view of a mechanism for adjusting position of the at least one fluid massage element for tricep massaging of the massage chair of FIG. 1.
Figure 19B:
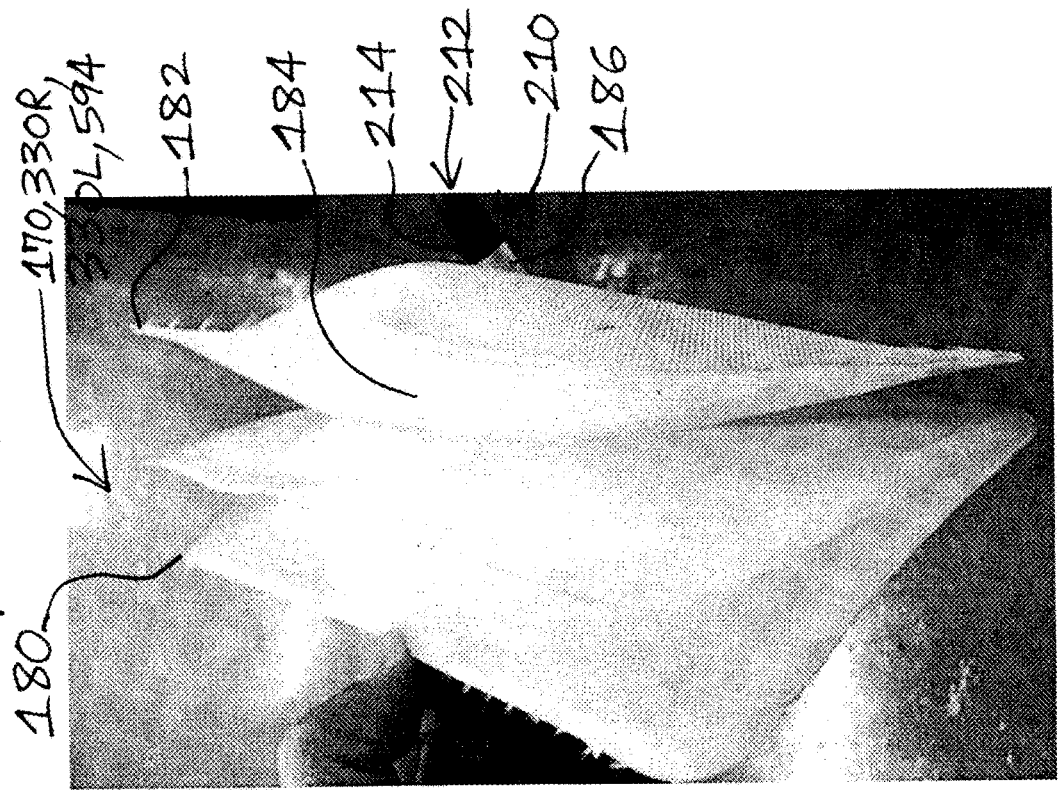
FIG. 19B is a perspective view of the fluid massage element and the fluid transport device of FIG. 19A.
Figure 19A:
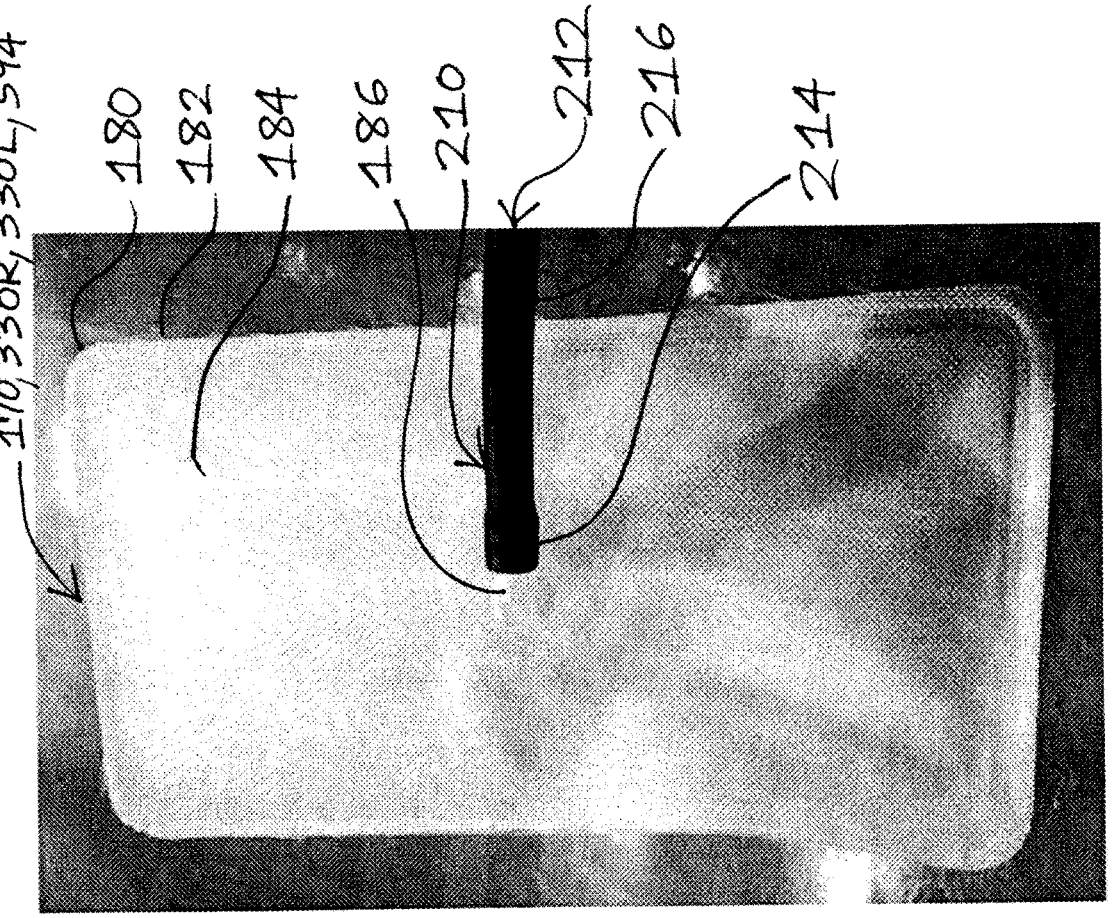
FIG. 19A is a side, perspective view of a fluid massage element and a fluid transport device of an arm massage system, a body massage system and a legs and feet massage system of the massage chair of FIG. 1.

As best shown in FIGS. 15 and 16, the mechanism 540R,540L for adjusting position of the at least one fluid massage element 534R,534L for tricep massaging provides adjustments to the at least one fluid massage element 534R, 534L for tricep massaging, respectively, such that massaging effects are able to be provided to corresponding triceps of a plurality of users who have different body sizes and different tricep sizes. As a non-limiting example, the mechanism 540R,540L is a tricep metal support device 540R,540L which comprises a mounting plate 542R,542L, a rotatable mechanism 546R,546L, a connecting body 550R,550L, and a rotatable hinge 554R,554L. Each of the mounting plate 542R,542L has a plurality of holes 543R,543L for receiving a plurality of screws 544R,544L for being mounted to the inner side 514R,514L of the arm panel 510R,510L, respectively. Each of the rotatable mechanism 546R,546L is rotatably secured to the mounting plate 542R,542L, respectively, and can be rotated in a circular motion or direction with respect to the mounting plate 542R,542L, respectively, to allow the position of the fluid massage elements 534R,534L, respectively, to be adjusted from the starting or first tricep massaging position to at least one other tricep massaging position and, preferably, vice versa and between all of these tricep massaging positions. Each of the connecting body 550R,550L has a first end 551R,551L and a second end 552R,552L, respectively, and is positioned between the rotatable mechanism 546R,546L and rotatable hinge 554R, 554L, respectively. Each of the rotatable hinge 554R,554L is rotatably secured to the second end 552R,552L of the connecting body 550R,550L, respectively, and can be rotated in an upward, angled motion or direction and, alternatively, in an downward, angled motion or direction, with respect to the second end 552R,552L and mounting plate 542R,542L, respectively, to allow the position of the fluid massage elements 534R,534L, respectively, to be adjusted from the starting or first tricep massaging position to at least one other tricep massaging position and, preferably, vice versa and between all of these tricep massaging positions.

As best shown in FIGS. 17 and 18, the mechanism 560R,560L for adjusting position of the at least one fluid massage element 536R,536L for shoulder massaging provides adjustments to the at least one fluid massage element 536R,536L for shoulder massaging, respectively, such that massaging effects are able to be provided to corresponding shoulders of a plurality of users who have different body sizes and different shoulder sizes. As a non-limiting example, the mechanism 560R,560L comprises a mounting plate 562R,562L, a rotatable mechanism 566R,566L, and a rotatable hinge 574R,574L. Each of the mounting plate 562R,562L has a plurality of holes 563R,563L for receiving a plurality of screws 564R,564L for being mounted to the inner side 514R,514L of the arm panel 510R,510L, respectively. Each of the rotatable mechanism 566R,566L is rotatably secured to the mounting plate 562R,562L, respectively, and can be rotated in a circular motion or direction with respect to the mounting plate 562R,562L, respectively, to allow the position of the fluid massage elements 536R,536L, respectively, to be adjusted from the starting or first shoulder massaging position to at least one other shoulder massaging position and, preferably, vice versa and between all of these shoulder massaging positions. Each of the rotatable hinge 574R,574L is rotatably secured to the mounting plate 562R, 562L, respectively, and can be rotated in an upward, angled motion or direction and, alternatively, in an downward, angled motion or direction, with respect to the mounting plate 562R,562L, respectively, to allow the position of the fluid massage elements 536R,536L, respectively, to be adjusted from the starting or first shoulder massaging position to at least one other shoulder massaging position and, preferably, vice versa and between all of these shoulder massaging positions.

Preferably, the arm massage system 530R,530L further comprises a fluid compressor or pump 190, a power source 220, at least one fluid valve device 200 for regulating fluid flow into and out of the at least one fluid massage element 532R,532L for hand massaging, at least one fluid transport device 210 for hand massaging, at least one fluid valve device 200 for regulating fluid flow into and out of the at least one fluid massage element 534R,534L for tricep massaging, at least one fluid transport device 210 for tricep massaging, at least one fluid valve device 200 for regulating fluid flow into and out of the at least one fluid massage element 536R,536L for shoulder massaging, at least one fluid transport device 210 for shoulder massaging, and a noise-reducing (or noise-absorbing, noise-containing or noise-cancelling), enclosure device 230.

As a non-limiting example, FIG. 20 shows a massage control flow chart for the plurality of fluid massage elements 532R,532L,534R,534L,536R,536L in an operating relationship with a remote control 580, a master control board 582, a power supply or source 220, at least one air compressor or pump 190, and an air valve bank 531.

Preferably, the fluid compressor or pump 190 pumps fluid into the plurality of fluid massage elements 180,532R,532L, 534R,534L,536R,536L such that massaging effects can be provided to the user at desired massage locations or pressure points. The fluid compressor or pump 190 comprises a fluid pump body 192, a fluid pump inlet 194, and a fluid pump outlet 196. The fluid compressor or pump 190 (such as the non-limiting example shown in FIGS. 25, 29 and 30) may be any fluid compressor or pump known to one of ordinary skill in the art that is able to pump air, a liquid, a gel, any fluid(s) known to one of ordinary skill in the art, and any combination thereof into the plurality of fluid massage elements 180,532R,532L,534R,534L,536R,536L.

The plurality of fluid valve devices 200 regulate fluid flow into and out of the plurality of fluid massage elements 180,532R,532L,534R,534L,536R,536L. Each of the fluid valve device 200 comprises a fluid valve body 202, a fluid valve inlet 204, and a fluid valve outlet 206. Each of the plurality of fluid valve devices 200 (such as the non-limiting example shown in FIGS. 25, 29 and 30) may be any fluid valve device known to one of ordinary skill in the art that is able to regulate fluid flow into and out of the corresponding fluid massage element(s) 180,532R,532L,534R, 534L,536R, 536L.

The plurality of fluid transport devices 210 transport fluid flow into and out of the plurality of fluid massage elements 180,532R,532L,534R,534L,536R,536L. Each of the plurality of fluid transport devices 210 (such as the non-limiting example shown in FIGS. 19A and 19B) may be any fluid transport device known to eRe-one of ordinary skill in the art that is able to transport fluid flow into and out of the corresponding fluid massage element(s) 180,532R,532L, 534R,534L,536R,536L. The fluid transport device 210 is a transport tube 210 having a tube first end 212, a tube second end 214, and a tube body 216 extending between the tube first end 212 and tube second end 214.

Figure 24:
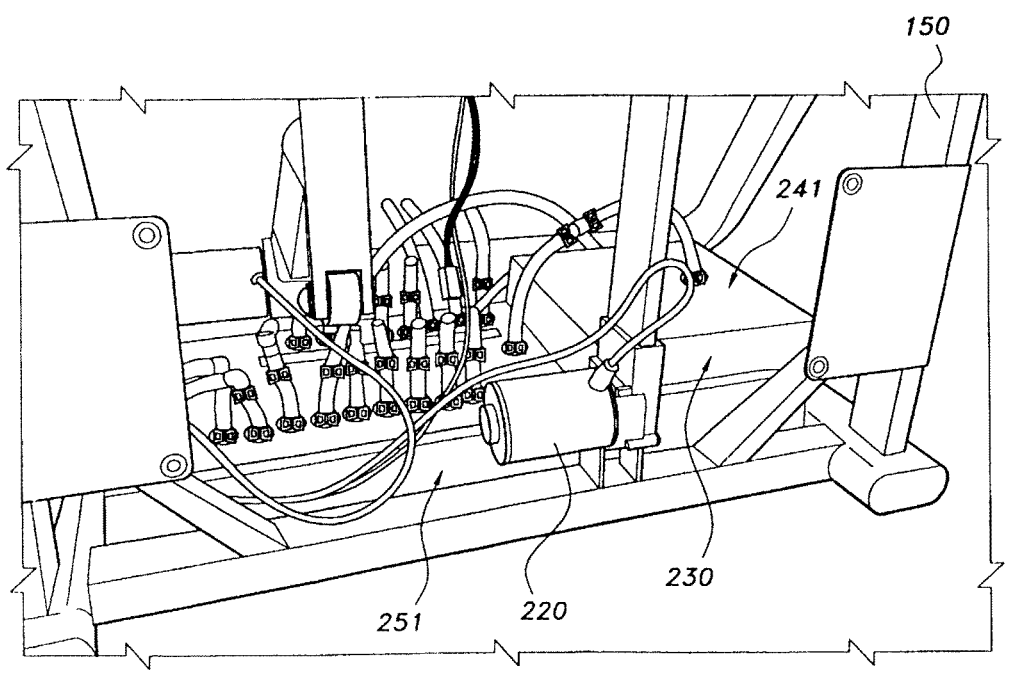
FIG. 24 is an internal rear, perspective view of a massage chair frame (with a noise-reducing chamber underneath the seat) and a massage system of the massage chair of FIG. 1.
Figure 25:
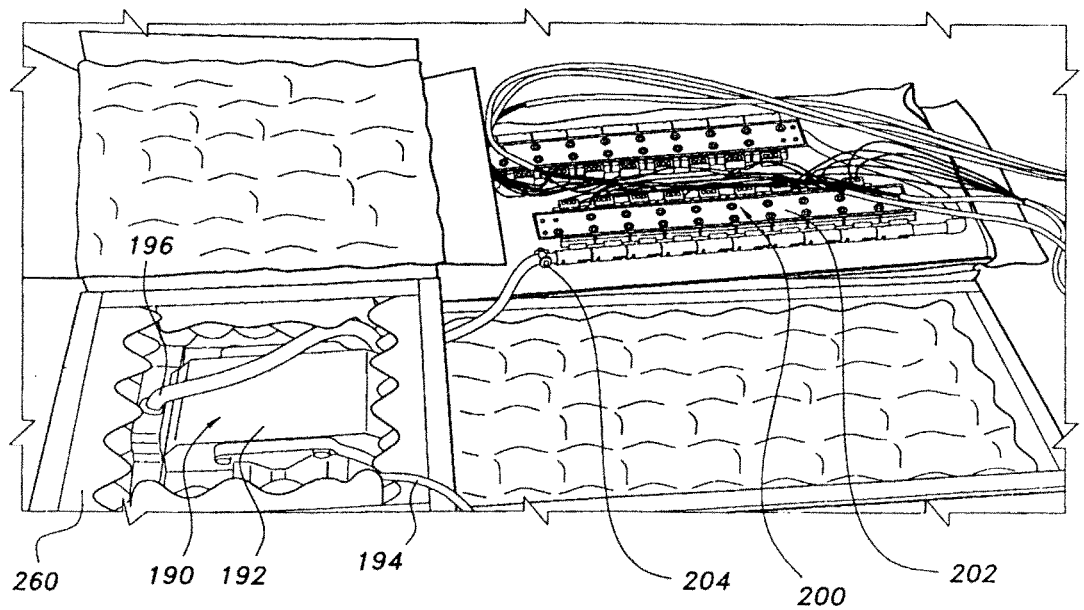
FIG. 25 is a top, perspective view of a massage system and a noise-reducing, enclosure device of the massage chair of FIG. 1.
Figure 26:
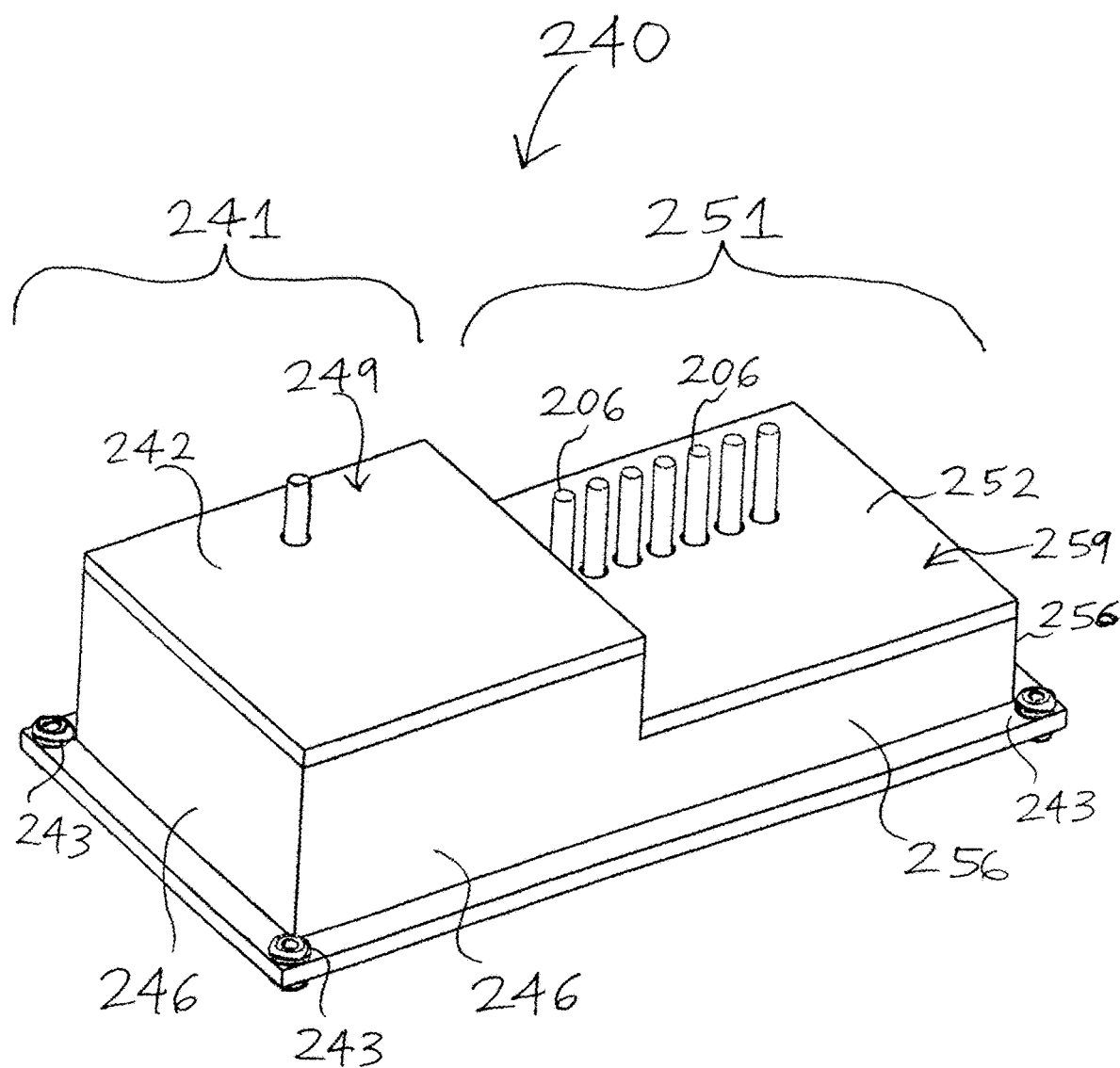
FIG. 26 is a top, perspective view of the noise-reducing, enclosure device of FIG. 25.
Figure 27:
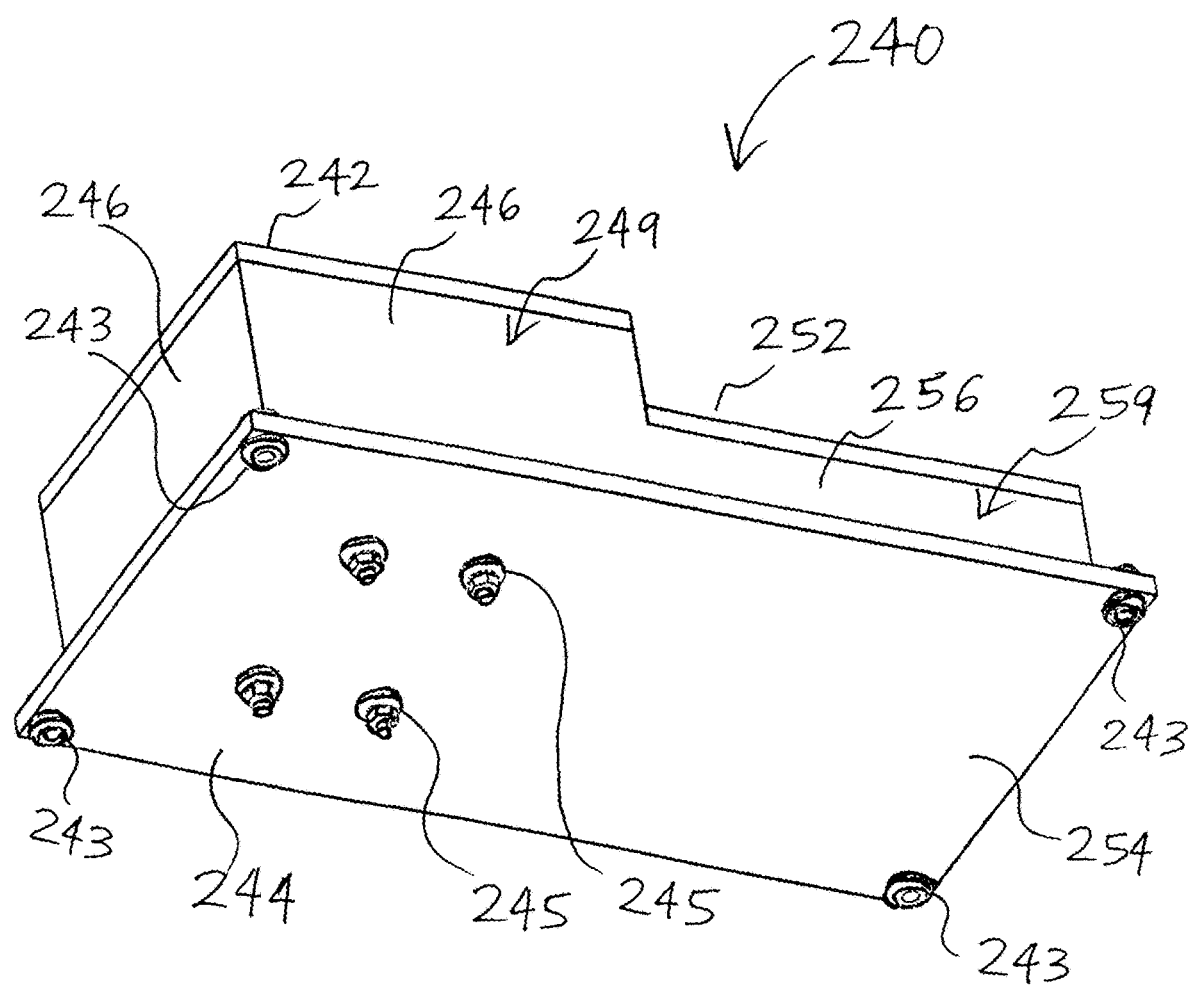
FIG. 27 is a bottom, perspective view of the noise-reducing, enclosure device of FIG. 25.
Figure 28:
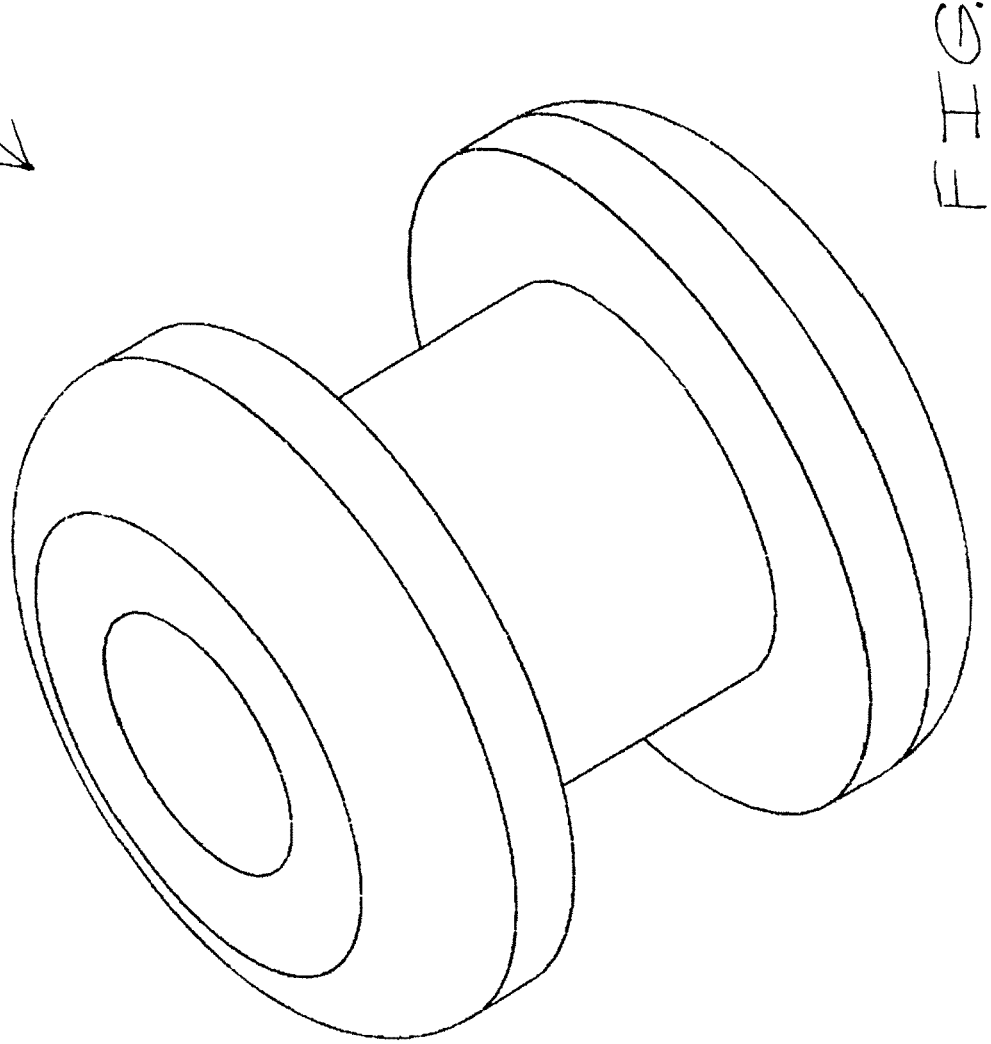
FIG. 28 is a perspective view of a vibration-reducing securing nut of the noise-reducing, enclosure device of FIG. 25.

As shown in FIG. 24, the power source 220 provides power to the fluid compressor or pump 190, and may also be used to provide power to other components of the massage chair 500. The power source 220 may be a battery, a connector or cord for plugging into a power outlet (such as, but not limited to, a detachable DC power supply cord), a plug for receiving power or electricity, any power source known to one of ordinary skill in the art, and any combination thereof.

As best shown in FIGS. 19A, 19B, 24 and 25, the body massage system 170 comprises at least one fluid massage element 180, a fluid compressor or pump 190, and at least one fluid valve device 200 for regulating fluid flow into and out of the at least one fluid massage element 180. Preferably, the body massage system 170 also comprises at least one fluid transport device 210 and a power source 220. Also preferably, the at least one fluid massage element 180 is a plurality of fluid massage elements 180, the at least one fluid valve device 200 is a plurality of fluid valve devices 200, and the at least one fluid transport device 210 is a plurality of fluid transport devices 210. The body massage system 170 is in operational communication with the massage chair frame 110 such that the body massage system 170 provides body massaging effects to a user (not shown) positioned in the massage chair 500.

Each of the plurality of fluid massage elements 180 of the body massage system 170 is adapted for having fluid transported or pumped into it by the fluid compressor or pump 190 and for having fluid withdrawn from it. The plurality of fluid massage elements 180 may be positioned at predetermined massage locations on, about, or in the vicinity of the massage chair frame 110 and/or may be moved or transported to desired massage locations by the user. The plurality of fluid massage elements 180 may be a plurality of fluid massage cells (such as, but not limited to, air cell 180 shown in FIGS. 19A and 19B), a plurality of fluid massage bags (such as, but not limited to, air bags), any fluid massage element(s) known to one of ordinary skill in the art, and any combination thereof. The air cell 180 comprises an inflatable or expandable air cell housing 182, an air cell chamber 184 defined by the air cell housing 182, and an air cell inlet and outlet 186. The fluid that is contained in and/or pumped into and out of the plurality of fluid massage elements 180 may be air, a liquid, a gel, any fluid(s) known to one of ordinary skill in the art, and any combination thereof.

As best shown in FIGS. 1-3, 4-7 and 22-23, the legs and feet massage apparatus 590 includes a legs and feet frame 592 and a legs and feet massage system 594. Preferably, the legs and feet frame 592 is secured to or about the first end 122R,122L of the massage chair frame 110 by a securing device 593 such that the legs and feet frame 592 extends forward of and downwardly from the first end 122R,122L of the massage chair frame 110.

The legs and feet massage system 594 comprises at least one fluid massage element 180, a fluid compressor or pump 190, and at least one fluid valve device 200 for regulating fluid flow into and out of the at least one fluid massage element 180. Preferably, the body massage system 170 also comprises at least one fluid transport device 210 and a power source 220. Also preferably, the at least one fluid massage element 180 is a plurality of fluid massage elements 180, the at least one fluid valve device 200 is a plurality of fluid valve devices 200, and the at least one fluid transport device 210 is a plurality of fluid transport devices 210. The legs and feet massage system 594 is in operational communication with the legs and feet frame 592 such that the legs and feet massage system 594 provides legs and feet massaging effects to a user (not shown) positioned in the massage chair 500.

Each of the plurality of fluid massage elements 180 of the legs and feet massage system 594 is adapted for having fluid transported or pumped into it by the fluid compressor or pump 190 and for having fluid withdrawn from it. The plurality of fluid massage elements 180 may be positioned at predetermined massage locations on, about, or in the vicinity of the legs and feet chair frame 592 and/or may be moved or transported to desired massage locations by the user. The plurality of fluid massage elements 180 may be a plurality of fluid massage cells (such as, but not limited to, air cell 180 shown in FIGS. 19A and 19B), a plurality of fluid massage bags (such as, but not limited to, air bags), any fluid massage element(s) known to one of ordinary skill in the art, and any combination thereof. The air cell 180 comprises an inflatable or expandable air cell housing 182, an air cell chamber 184 defined by the air cell housing 182, and an air cell inlet and outlet 186. The fluid that is contained in and/or pumped into and out of the plurality of fluid massage elements 180 may be air, a liquid, a gel, any fluid(s) known to one of ordinary skill in the art, and any combination thereof.

To be efficient and keep the cost low as possible, it is preferred that the arm massage system 530R,530L, body massage system 170, and legs and feet massage system 594 share as many components, such as the fluid compressor or pump 190, power source or supply 220, etc., as possible.

As best shown in FIGS. 24-31, the noise-reducing (or noise-absorbing, noise-containing, or noise-cancelling), enclosure device 230 comprises an enclosure housing 240 and noise-reducing (or noise-absorbing, noise-containing, or noise-cancelling) material 260 positioned inside the enclosure housing 240. The enclosure housing 240 encloses the fluid compressor or pump 190 and the plurality of fluid valve devices 200 during operation. The noise-reducing, enclosure device 230 is preferably positioned in proximity of the massage chair frame 110. As a non-limiting example shown in FIG. 24, the noise-reducing, enclosure device 230 is positioned below the seat or bottom body area portion 126R,126L of the massage chair frame 110.

As a non-limiting example and as best shown in FIGS. 25-31, the enclosure housing 240 has a first section 241 that comprises a top 242, a bottom 244, a plurality of sides 246, an inner surface 248, and an outer surface 249, and a second section 251 that comprises a top 252, a bottom 254, a plurality of sides 256, an inner surface 258, and an outer surface 259. Preferably, the inner surfaces 248,258 and noise-reducing (or noise-absorbing, noise-containing, or noise-cancelling) material 260 help to form noise-reducing (or noise-absorbing, noise-containing, or noise-cancelling) walls for the enclosure housing 240. The first section 241 of the enclosure housing 240 encloses (partially, substantially, or fully encloses) the fluid compressor or pump 190 while the second section 251 of the enclosure housing 240 encloses (partially, substantially, or fully encloses) the plurality of fluid valve devices 200 such that noise generated from or made by the fluid compressor or pump 190 and the plurality of fluid valve devices 200 during operation is reduced, contained or eliminated. The enclosure housing 240 also has a plurality of foot elements 243 positioned at predetermined locations on the periphery of the enclosure housing 240, and a plurality of screw and nut elements 245 positioned at predetermined locations.

Figure 29:
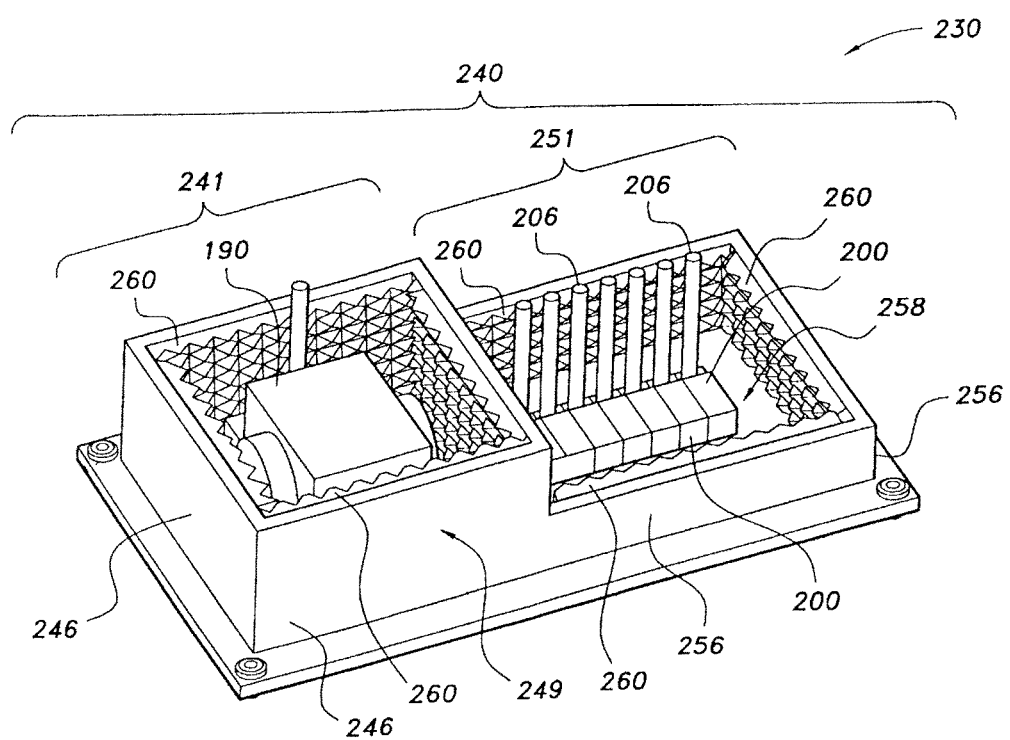
FIG. 29 is an internal top, perspective view of the massage system and the noise-reducing, enclosure device of FIG. 25, with a top of the noise-reducing, enclosure device being temporarily removed.
Figure 30:
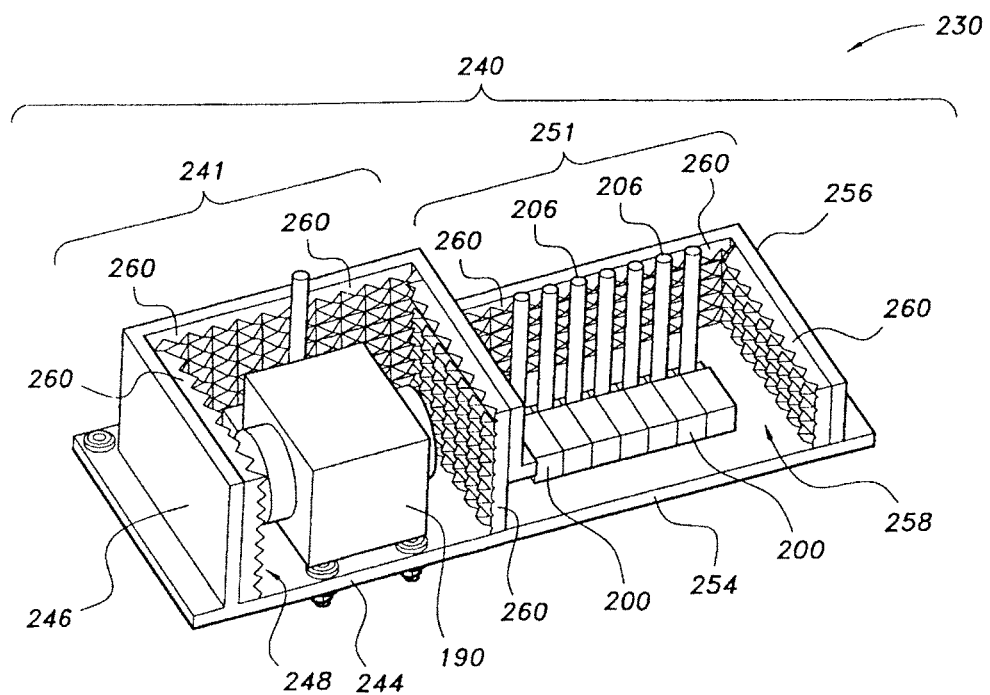
FIG. 30 is a partial cut-away, top, perspective view of the massage system and the noise-reducing, enclosure device of FIG. 25, with a top of the noise-reducing, enclosure device being temporarily removed.
Figure 31:
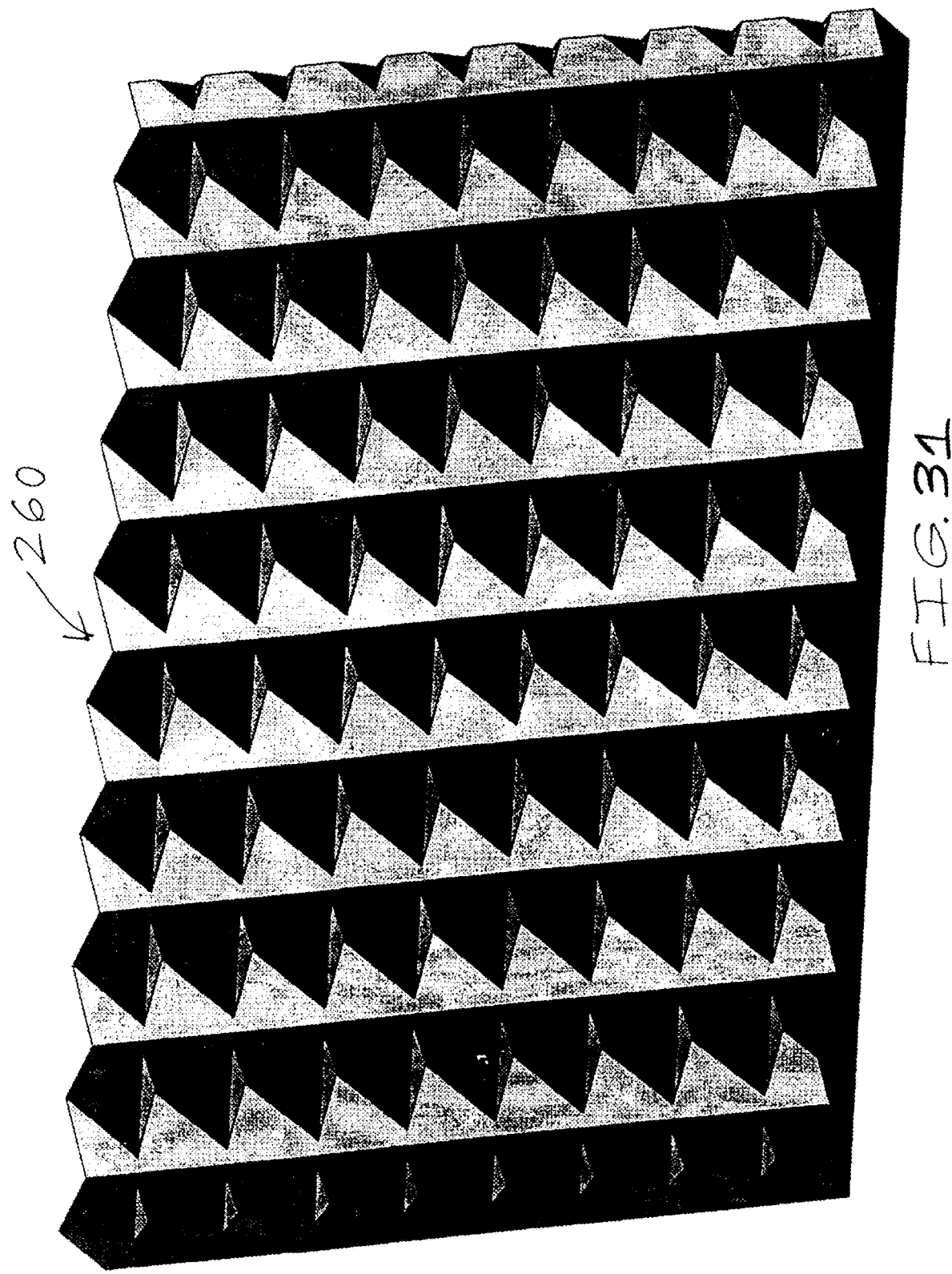
FIG. 31 is a perspective view of noise-reducing material of the noise-reducing, enclosure device of FIG. 25.
Figure 32:
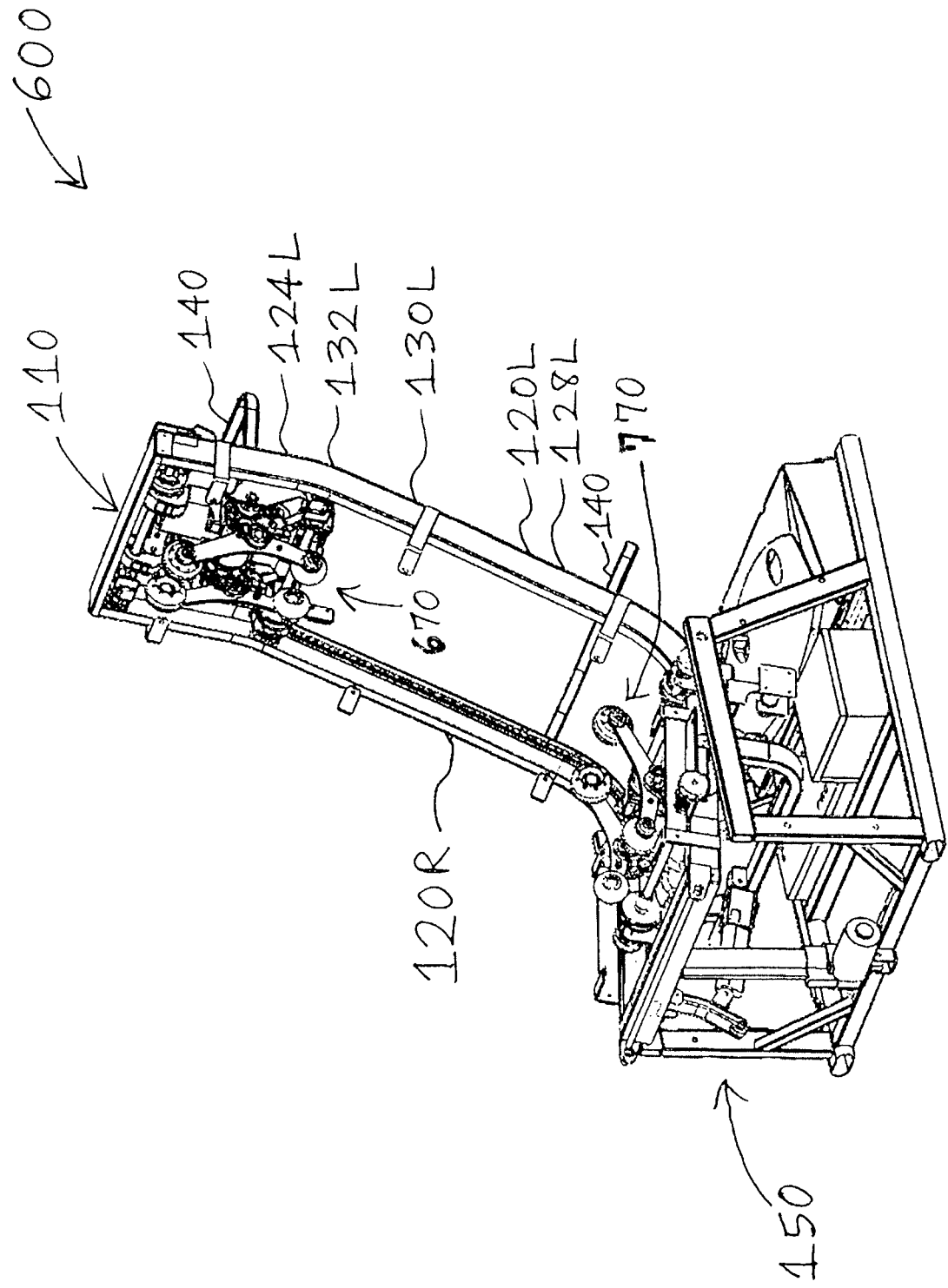
FIG. 32 is a perspective, front and left side view of another body massage system being secured to a massage frame of a massage chair according to the present invention.
Figure 33:
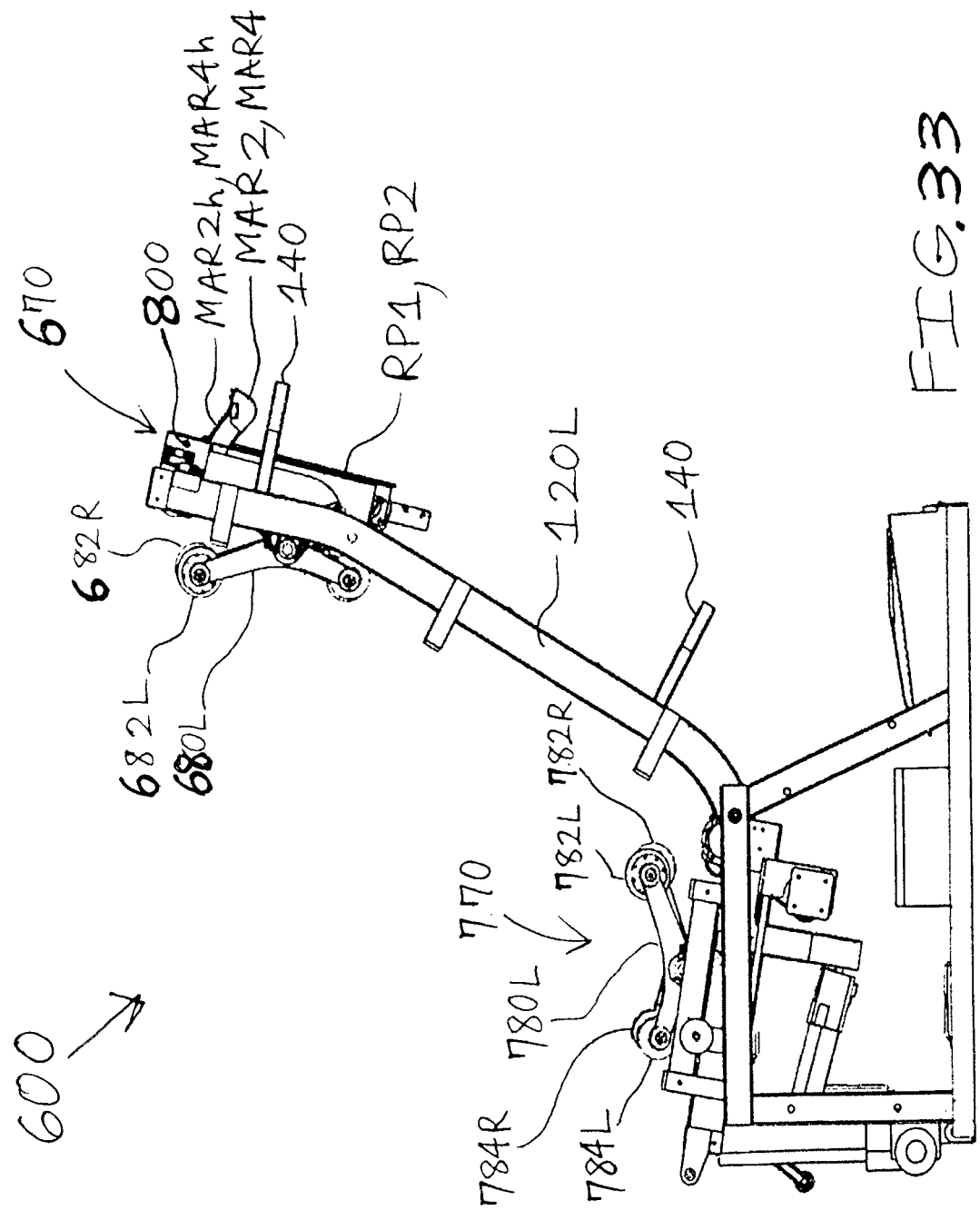
FIG. 33 is a left side view of the body massage system being secured to the massage frame of the massage chair of FIG. 32.
Figure 34:
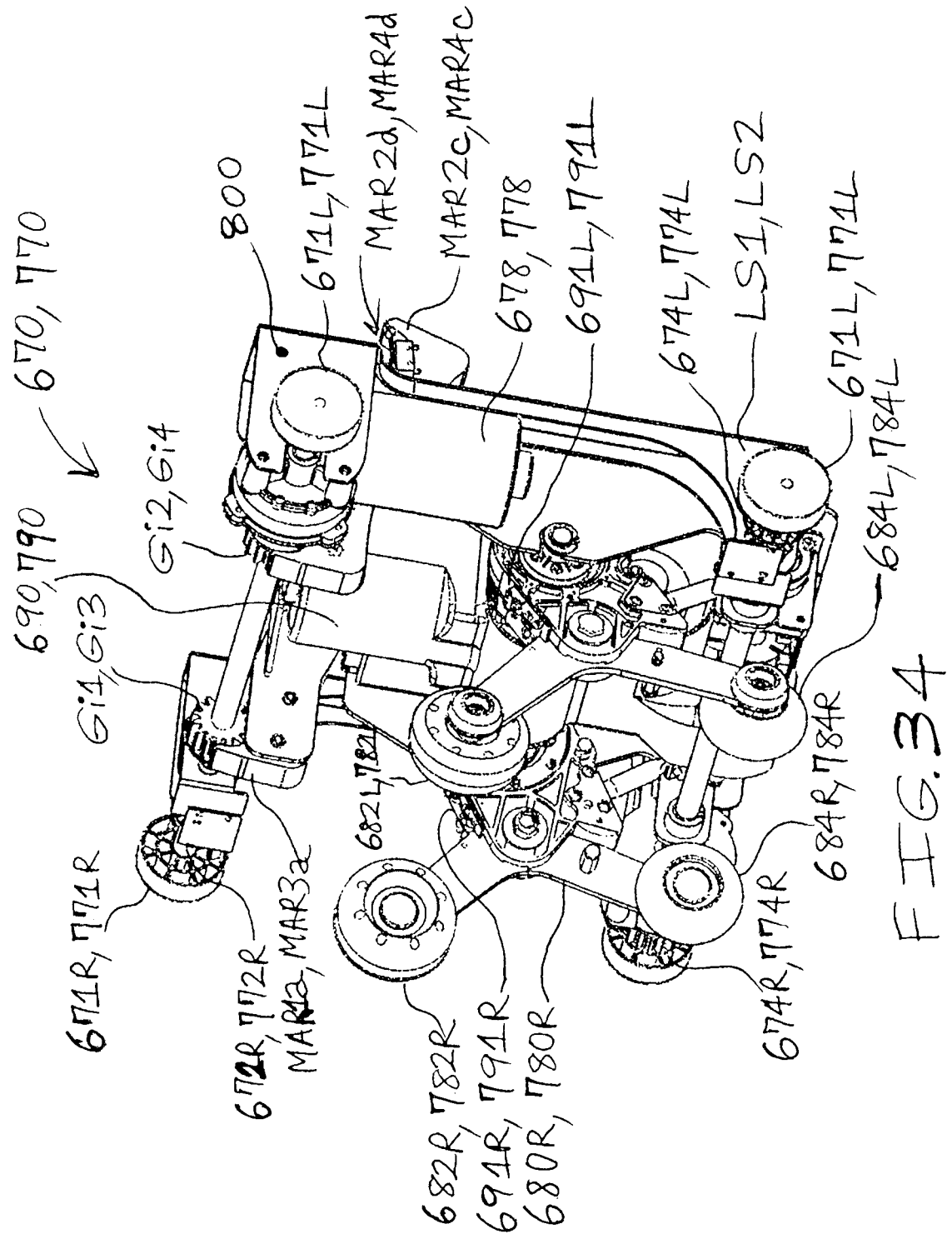
FIG. 34 is a perspective, front and left side view of the body massage device of the massage chair of FIG. 32.
Figure 35:
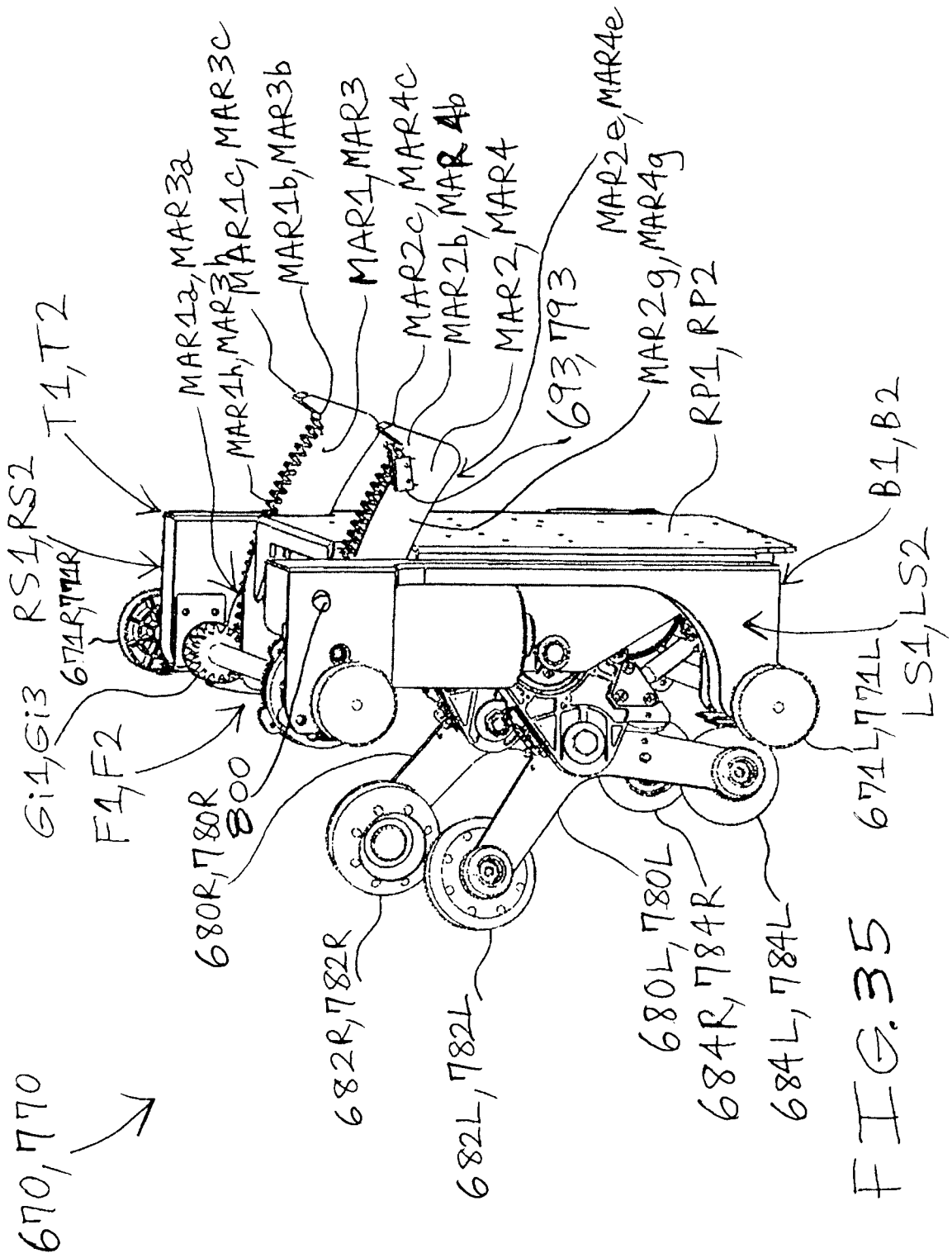
FIG. 35 is a perspective, left side view of the body massage device of FIG. 34.
Figure 36:
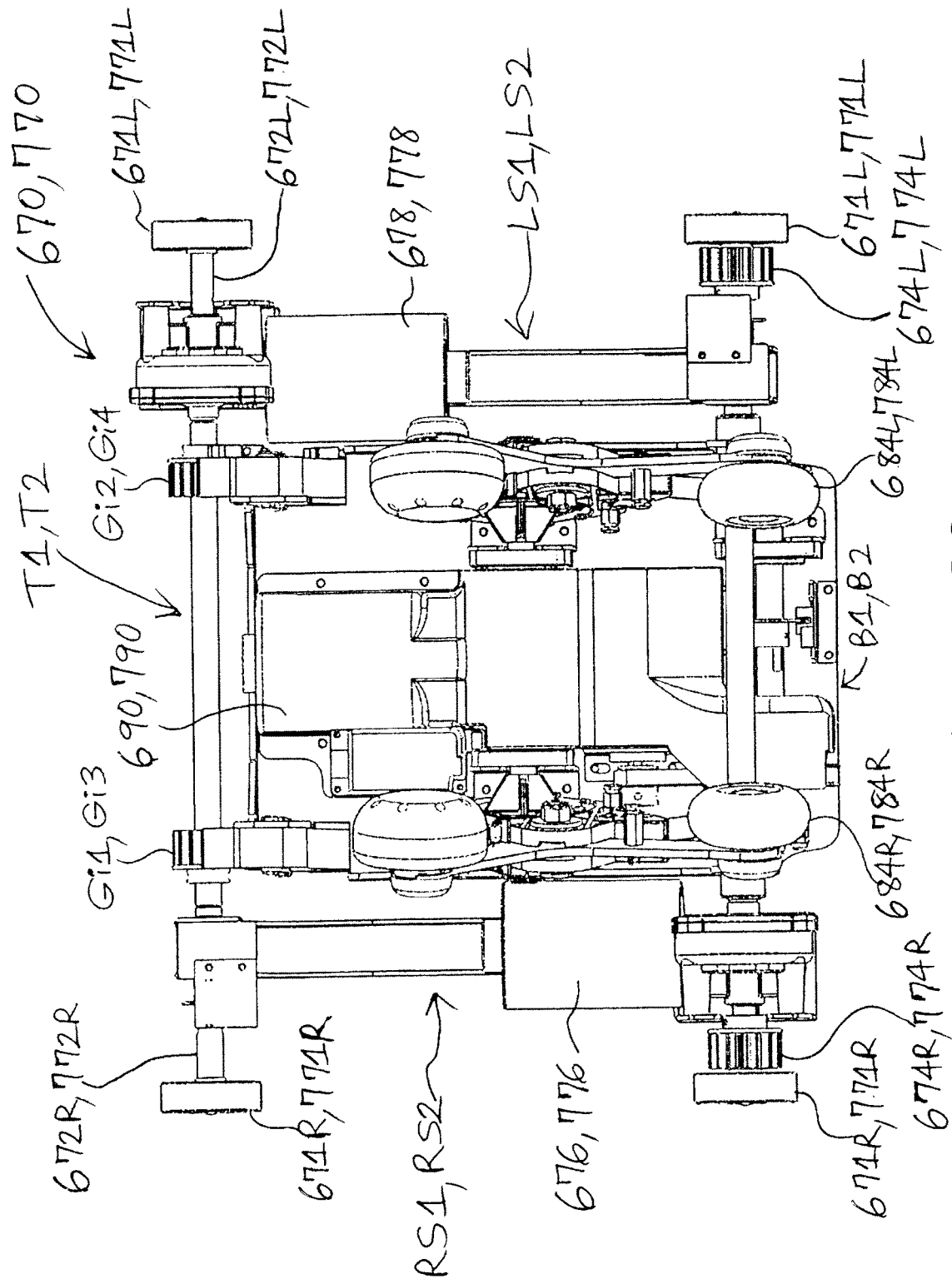
FIG. 36 is an elevated, front view of the body massage device of FIG. 34.

Preferably, the noise-reducing (or noise-absorbing, noise-containing, or noise-cancelling) material 260 is positioned inside the enclosure housing 240 in such a way that it surrounds the fluid compressor or pump 190 and the plurality of fluid valve devices 200 such that noise generated from or made by the fluid compressor or pump 190 and the plurality of fluid valve devices 200 during operation is reduced, contained or eliminated. Preferably, as shown in FIGS. 29 and 30, all of the inner surfaces 248,258 of the enclosure housing 240 are covered by the noise-reducing material 260. Preferably, all of the electro-mechanical components positioned inside the enclosure housing 240 are fully surrounded by the noise-reducing material 260. The noise-reducing material 260 may be foam, noise-reducing foam, noise-absorbing foam, noise-containing foam, noise-cancelling foam, any noise-reducing material known to one of ordinary skill in the art, any noise-absorbing material known to one of ordinary skill in the art, any noise-containing material known to one of ordinary skill in the art, any noise-cancelling material known to one of ordinary skill in the art, and any combination thereof.

When in use or in operation, the user (not shown) may activate at least one of the arm massage system 530R,530L, body massage system 170, and legs and feet massage system 594 of the massage chair 500 by or via pushing, touching, using voice command for use on or with, using a mechanical or remote control for use on or with, or any other activation method known to one of ordinary skill in the art, an activation, start, control or command button, touch area, box or panel, or any other activation method or element known to one of ordinary skill in the art. Preferably, the user is able to control the massage producing-effects of the plurality of fluid massage elements 180 such that the plurality of fluid massage elements 180 provide massage producing-effects to a desired body part area(s), such as the hands, triceps, shoulders, thighs, bottom, lower back, upper back, head and neck, lower leg, and/or feet of the user so that desired body part area(s) of the user can receive massage effects or benefits from the plurality of fluid massage elements 180 when desired.

As a non-limiting example of a second embodiment (shown in FIGS. 1-7 and 11-37), it is preferred that the massage chair 600 of the second embodiment is substantially the same as the massage chair 500 of the first embodiment, except that the body massage system 170 of the first embodiment is replaced by at least one body massage device 670,770 of the second embodiment that allows a user to adjust the intensity and position of a massage. In addition, the massage chair 600 may also comprise or include a collision-sensing system or device 800.

The at least one body massage element (such as, but not limited to, massage arm or member 680R,680L,780R,780L) of at least one body massage device 670,770 is able to move in three-dimensional (3-D) directions. The massage element 680R,680L,780R,780L can be set to any position within the limits of the massage chair 600. When the massage chair 600 includes more than one body massage device 670,770 and each body massage device 670,770 has more than one massage element 680R,680L,780R,780L, it is preferred that each massage element 680R,680L,780R,780L of at least one body massage device 670,770 is able to move in 3-D directions, and also preferred that the body massage devices 670,770 are able to travel or be moved along a track (such as, but not limited to, guide rail(s) 120R,120L) at or about the same time. In addition, the collision-sensing system or device 800 preferably includes or is in operational communication with collision control software to control the body massage devices 670,770 so as to prevent collisions between the body massage devices 670,770.

With regard to the first body massage device 670 and second body massage device 770 (as best shown in FIGS. 32-37), it is preferred that the body massage devices 670,770 are substantially or exactly the same as one another. It is also preferred that each massage element (such as, but not limited to, massage arm or member 680R,680L,780R,780L) of each body massage device 670,770 is able to move in 3-D directions, and that the body massage devices 670,770 are able to travel or be moved along the guide rail(s) 120R,120L at or about the same time. As a non-limiting example, the first body massage device 670 and second body massage device 770 may be positioned, initially or when they are not in operation, about the first end and second end of the guide rails 120R,120L, respectively, and then they can move or be moved toward (or away from, when applicable) one another along the guide rails 120R,120L during operation. Thus, in combination with each other and via their massage elements 680R,680L,780R,780L, the first body massage device 670 and second body massage device 770 are preferably able to provide massage benefits or effects to more than one body area, such as a back body area, a bottom body area, a thigh body area, and a head and neck body area, of the user at or about the same time.

Each of the first body massage device 670 and second body massage device 770 generally includes at least one massage element (such as, but not limited to, a massage arm or member 680R,680L,780R,780L); at least one power source (such as, but not limited to, a power inlet, a battery or a motor) for powering or driving the body massage device 670,770 along the guide rails 120R,120L, for powering or driving the massage arm(s) or member(s) 680R,680L,780R, 780L in an in-and-out motion, and for powering or driving the massage arm(s) or member(s) 680R,680L,780R,780L with regard to an intensity motion); a mechanism (such as, but not limited to, at least one massage arm rail MAR1, MAR2,MAR3,MAR4) for allowing the massage element 680R,680L, 780R,780L to produce the in-and-out motion; a mechanism for allowing the massage element 680R,680L, 780R,780L to produce the intensity motion; and a mechanism (such as, but not limited to, at least one gear member) for operationally engaging with the guide rails 120R,120L.

As a non-limiting example and as best shown in FIGS. 32-37, each of the first and second body massage devices 670,770 includes a front F1,F2, a rear plate RP1,RP2, a right side RS1,RS2, a left side LS1,LS2, a top T1,T2, a bottom 61,62, a pair of massage arm rails MAR1,MAR2,MAR3, MAR4, a pair of gear devices Gi1,Gi2,Gi3,Gi4 driven by a motor to control the intensity motion of the massage arms, four supporting wheels 671R,671L,771R,771L, a pair of massage device moving members 672R,672L,772R,772L, a pair of guide rail gear members 674R,674L,774R,774L, a pair of massage arms or members 680R,680L,780R,780L, a first motor 676,776, a second motor 678,778, a third motor 690,790, a pair of position sensing devices 691R,691L, 791R,791L, and a pair of limit sensing devices 692,693,792, 793.

Preferably, each massage arm rail of the corresponding pair of massage arm rails MAR1,MAR2,MAR3,MAR4 is substantially similar to or exactly the same as the other massage arm rail of that corresponding pair. More preferably, each massage arm rail of the massage arm rails MAR1,MAR2,MAR3,MAR4 is substantially similar to or exactly the same as one another. Each of the massage arm rails MAR1,MAR2,MAR3,MAR4 includes a first end MAR1$a$,MAR2$a$,MAR3$a$, MAR4$a$, a second end MAR1$b$, MAR2$b$,MAR3$b$,MAR4$b$ with a stop member MAR1$c$, MAR2$c$,MAR3$c$,MAR4$c$, a top MAR1$d$,MAR2$d$,MAR3$d$, MAR4$d$, a bottom MAR1$e$,MAR2$e$,MAR3$e$,MAR4$e$, a first side MAR1$f$,MAR2$f$,MAR3$f$,MAR4$f$, a second side MAR1$g$,MAR2$g$,MAR3$g$,MAR4$g$, and gear teeth MAR1$h$, MAR2$h$, MAR3$h$,MAR4$h$ located about the top MAR1$d$, MAR2$d$,MAR3$d$,MAR4$d$. The gear teeth MAR1$h$,MAR2$h$, MAR3$h$,MAR4$h$ of the massage arm rails MAR1,MAR2, MAR3,MAR4 engage with corresponding gear devices Gi1, Gi2,Gi3,Gi4 from corresponding massage devices 170,270 to control the intensity motion of the massage arms 680R, 680L,780R,780L.

Each of the four supporting wheels 671R,671L,771R, 771L and of the massage device moving members 672R, 672L,772R,772L is positioned within a corresponding guide channel 136 of a guide rail 120R,120L, and helps the body massage devices 670,770 move in a generally vertical direction along the guide channel 136.

Each of the guide rail gear members 674R,674L,774R, 774L is positioned within a corresponding guide channel 136 of a guide rail 120R,120L, and engages with the teeth 138 located in the corresponding guide channel 136.

Each of the massage arms 680R,680L,780R,780L includes a first or upper massage roller 682R,682L,782R, 782L and a second or lower massage roller 684R,684L, 784R,784L. Preferably, each of the massage arms 680R, 680L, 780R,780L is able to move in 3-D directions. This means that each of the massage arms 680R,680L,780R,780L is able to move laterally (in an x-axis direction, or side to side direction of the body of a user), vertically (in a y-axis direction, or head to toe direction of the body of a user), and in-and-out (in a z-axis direction, or front to back direction of the body of a user). The massage rollers 682R,682L,782R, 782L,684R,684L,784R,784L provide massage benefits or effects to a back body area, a bottom body area, and a thigh body area of the user when the body massage devices 670,770 are moved to, near or about that particular body area. The massage rollers 682R,682L,782R,782L,684R, 684L, 784R,784L may also provide massage benefits or effects to a head and neck area of the user when the body massage devices 670,770 are moved to, near or about the head and neck area. It will be understood by one of ordinary skill in the art that the timing of the pattern of the movement, such as raising and lowering, of the rollers 682R,682L, 782R,782L,684R,684L,784R,784L in any, some or all of the 3-D directions may be varied on each roller 682R,682L, 782R,782L, 684R,684L,784R,784L. These rollers 682R, 682L,782R,782L,684R,684L, 784R,784L can move in 3-D directions by controlling the three motors: the first motor 676,776, the second motor 678,778, and the third motor 690,790.

Each first motor 676,776 is preferably positioned toward the front F1,F2 and on the right side RS1,RS2 of the corresponding body massage device 670,770, and is in operational communication with the corresponding pair of the massage arms 680R,680L,780R,780L such that it causes or drives the up-and-down motion of the corresponding pair of the massage arms 680R,680L, 780R,780L. Also, the body massage devices 670,770 travel or are moved along the guide rails 120R,120L via gears 674R,674L,774R,774L and first motor 676,776.

Each second motor 678,778 is preferably positioned toward the front F1,F2 and on the left side LS1,LS2 of the corresponding body massage device 670,770, and is in operational communication with the corresponding pair of the massage arms 680R,680L,780R,780L such that it causes or drives the intensity motion of the corresponding pair of massage arms 680R,680L,780R,780L.

Each third motor 690,790 is preferably positioned toward the front F1,F2 and top T1,T2 of the corresponding body massage device 670,770, and is in operational communication with the corresponding pair of the massage arms 680R,680L,780R,780L such that it causes or drives the in-and-out motion of the corresponding pair of the massage arms 680R,680L,780R,780L.

Each pair of position sensing devices 691R,691L,791R, 791L are preferably positioned about the corresponding upper massage rollers 682R,682L,782R,782L of the corresponding massage arms 680R,680L,780R,780L, and are for detecting the user's body contour and shoulder position.

Each pair of limit sensing devices 692,693,792,793 are preferably positioned about the corresponding first end MAR1$a$,MAR2$a$,MAR3$a$,MAR4$a$ and corresponding second end MAR1$b$,MAR2$b$,MAR3$b$,MAR4$b$ of the corresponding massage arm rails MAR2,MAR4, and are for detecting the maximum to minimum position points as the massage arms 680R,680L,780R,780L move forward and rearward (or "in and out") via the massage arm rails MAR1, MAR2,MAR3,MAR4 moving forward and rearward relative to the positions of the gear devices Gi1, Gi2,Gi3,Gi4 of the corresponding body massage device 670,770.

The collision-sensing system or device 800 preferably is positioned on one or both of the body massage devices 670,770, and preferably includes or is in operational communication with collision control software to control the body massage devices 670,770 so as to prevent collisions between the body massage devices 670,770. In addition, the collision-sensing system or device 800 preferably includes or is in operational communication with control software that prevents or stops the body massage devices 670,770 from exiting or going out of the guide rails 120R,120L at the first and second ends 122R,122L,124R,124L of the guide rails 120R,120L.

When in use or in operation, the user (not shown) preferably activates both of the body massage devices 670,770 of the massage chair 600 by or via pushing, touching, using voice command for use on or with, using a mechanical or remote control for use on or with, or any other activation method known to one of ordinary skill in the art, an activation, start, control or command button, touch area, box or panel, or any other activation method or element known to one of ordinary skill in the art. Preferably, the user is able to control the generally vertical movement of the body massage devices 670,770 and massage rollers 682R,682L, 684R,684L,782R,782L,784R,784L upward and downward along the guide rails 120R,120L such that the body massage devices 670,670 and massage rollers 682R,682L,684R, 684L,782R,782L,784R,784L are positioned about, near or at a desired body part area, such as the thighs, bottom, lower back, upper back, and head and neck, of the user so that desired body part area of the user can receive massage effects or benefits from the massage rollers 682R,682L, 684R,684L,782R,782L,784R,784L when desired and with the desired intensity and/or with the desired in-and-out motion. Preferably, the user is also able to control the timing, movement, etc. of the massage rollers 682R,682L, 684R, 684L,782R,782L,784R,784L such that that the massage rollers 682R,682L,684R,684L,782R,782L,784R,784L can provide massage effects or benefits to different desired body part areas of the user at or about the same time and with the desired intensity and/or with the desired in-and-out motion.

It is to be understood that the present invention is not limited to the embodiments described above or as shown in the attached figures, but encompasses any and all embodiments within the spirit of the invention.

What is claimed is:

1. A massage chair comprising:
   a seat;
   a body;
   a body massage system in operational communication with said body of said massage chair; and
   at least one arm massage system comprising at least one fluid-actuated massage element for tricep massaging and a device for adjusting position of said at least one fluid-actuated massage element for tricep massaging,
   wherein said device for adjusting position of said at least one fluid-actuated massage element for tricep massaging comprises a first portion, a second portion, and a rotatable mechanical joint,
   wherein said first portion of said device for adjusting position of said at least one fluid-actuated massage element for tricep massaging is stationary and mounted to said body of said massage chair, and
   wherein said second portion of said device for adjusting position of said at least one fluid-actuated massage element for tricep massaging is rotatable on said first portion of said device for adjusting position of said at least one fluid-actuated massage element for tricep massaging via said rotatable mechanical joint around an axis for accommodating body length and body size of a user.

2. The massage chair according to claim 1, wherein said at least one fluid-actuated massage element for tricep massaging is selected from the group consisting of an air cell, an air bag, a liquid cell, a liquid bag, a gel cell, a gel bag, and any combination thereof.

3. The massage chair according to claim 1, wherein said first portion of said device for adjusting position of said at least one fluid-actuated massage element for tricep massaging is a mounting plate and said second portion of said device for adjusting position of said at least one fluid-actuated massage element for tricep massaging is an adjustable arm that holds said at least one fluid-actuated massage element.

4. The massage chair according to claim 3, wherein said adjustable arm is rotatable in a circular motion or direction with respect to said mounting plate.

5. The massage chair according to claim 4, wherein said adjustable arm is rotatable in steps defined by an array of holes or position holding elements.

6. The massage chair according to claim 1, wherein said at least one arm massage system is a right arm massage system and a left arm massage system.

7. The massage chair according to claim 1, wherein said at least one fluid-actuated massage element for tricep massaging is configured to be adjacent to a body of the user and comprises a first side and a second side, and wherein, during operation, said first side of said at least one fluid-actuated massage element for tricep massaging is in contact with a corresponding tricep of the user.

8. The massage chair according to claim 1, further comprising a thigh body area portion, wherein said thigh body area portion is located forward of said seat, wherein said body massage system comprises at least one massage element for body massaging, and wherein, during operation, said at least one massage element for body massaging provides massaging effects to at least a back body area of the user.

9. The massage chair according to claim 8, wherein said at least one massage element for body massaging is at least one fluid massage element, and wherein said body massage system further comprises at least one fluid valve device for regulating fluid flow into and out of said at least one fluid massage element, and at least one fluid transport device for transporting fluid flow into and out of said at least one fluid massage element.

10. The massage chair according to claim 8, further comprising a legs and feet massage system and a pair of guide rails, wherein said legs and feet massage system comprises at least one massage element for legs and feet massaging, wherein each of said pair of guide rails comprises a guide channel, wherein said guide channel comprises a plurality of gear teeth, and wherein during operation said at least one massage element for body massaging travels along said guide channel from said body to said seat and vice versa.

11. The massage chair according to claim 1, further comprising at least one guide rail,
   wherein each of said at least one guide rail comprises a guide rail first end, a guide rail second end, a guide rail thigh body area portion located about said guide rail first end, a guide rail seat body area portion located proximate said guide rail thigh body area portion and away from said guide rail first end, a guide rail back body area portion extending upward from said guide rail seat body area portion, a guide rail outer side, a guide rail inner side, and a guide channel extending from said guide rail thigh body area portion through said guide rail back body area portion, wherein each guide channel correspondingly runs along at least one of said guide rail inner side and said guide rail outer side of a corresponding guide rail of said at least one guide rail, and wherein at least one guide channel of said guide channel of said at least one guide rail comprises gear teeth.

12. The massage chair according to claim 1, wherein said body of said massage chair comprises a backrest.

13. The massage chair according to claim 12, wherein said body of said massage chair comprises an armrest and a footrest.

14. The massage chair according to claim 1, wherein said body of said massage chair comprises a footrest.

15. The massage chair according to claim 1, wherein said device for adjusting position of said at least one fluid-actuated massage element for tricep massaging is movable along at least two axes selected from the group consisting of an x axis, a y axis, and a z axis.

16. The massage chair according to claim 1, wherein at least one of said at least one arm massage system further comprises at least one massage element for shoulder massaging, and wherein, during operation, said at least one massage element for shoulder massaging provides massaging effects to a corresponding shoulder of the user.

17. The massage chair according to claim 16, wherein at least one of said at least one arm massage system further comprises at least one massage element for hand massaging, and wherein, during operation, said at least one massage element for hand massaging provides massaging effects to a corresponding hand of the user.

18. The massage chair according to claim 16, further comprising a massage chair frame and a device for securing said at least one arm massage system about said massage chair frame, wherein said at least one arm massage system is secured about said massage chair frame.

19. The massage chair according to claim 1, wherein at least one of said at least one arm massage system further comprises at least one massage element for hand massaging, and wherein, during operation, said at least one massage element for hand massaging provides massaging effects to a corresponding hand of the user.

20. The massage chair according to claim 1, further comprising a massage chair frame and a device for securing said at least one arm massage system about said massage chair frame, wherein said at least one arm massage system is secured about said massage chair frame.

21. The massage chair according to claim 20, wherein said massage chair frame comprises a right side and a left side, wherein said at least one arm massage system is a right arm massage system and a left arm massage system, and wherein said device for securing said at least one arm massage system is a first device for securing said right arm massage system to said right side of said massage chair frame and is a second device for securing said left arm massage system to said left side of said massage chair frame.

22. The massage chair according to claim 20, further comprising a legs and feet frame and a legs and feet massage system, wherein said legs and feet massage system comprises at least one massage element for legs and feet massaging, wherein said massage chair frame further comprises a pair of guide rails, wherein each of said pair of guide rails comprises a guide channel, wherein said guide channel comprises a plurality of gear teeth, and wherein during operation said at least one massage element for body massaging travels along said guide channel from said body to said seat body and vice versa.

23. The massage chair according to claim 1, further comprising a noise-reducing, enclosure device that comprises an enclosure housing.

24. A massage chair comprising:
a seat;
a body;
a body massage system in operational communication with said body of said massage chair; and
at least one arm massage system comprising at least one fluid-actuated massage element for shoulder massaging and a device for adjusting position of said at least one fluid-actuated massage element for shoulder massaging,
wherein said device for adjusting position of said at least one fluid-actuated massage element for shoulder massaging comprises a first portion, a second portion, and a rotatable mechanical joint,
wherein said first portion of said device for adjusting position of said at least one fluid-actuated massage element for shoulder massaging is stationary and mounted to said body of said massage chair, and
wherein said second portion of said device for adjusting position of said at least one fluid-actuated massage element for shoulder massaging is rotatable on said first portion of said device for adjusting position of said at least one fluid-actuated massage element for shoulder massaging via said rotatable mechanical joint around an axis for accommodating body length and body size of a user.

25. The massage chair according to claim 24, wherein said at least one fluid-actuated massage element for shoulder massaging is selected from the group consisting of an air cell, an air bag, a liquid cell, a liquid bag, a gel cell, a gel bag, and any combination thereof.

26. The massage chair according to claim 24, wherein said first portion of said device for adjusting position of said at least one fluid-actuated massage element for shoulder massaging is a mounting plate and said second portion of said device for adjusting position of said at least one fluid-actuated massage element for shoulder massaging is an adjustable arm that holds said at least one fluid-actuated massage element.

27. The massage chair according to claim 26, wherein said adjustable arm is rotatable in a circular motion or direction with respect to said mounting plate.

28. The massage chair according to claim 27, wherein said adjustable arm is rotatable in steps defined by an array of holes or position holding elements.

29. The massage chair according to claim 24, wherein said at least one fluid-actuated massage element for shoulder massaging is configured to be adjacent to a body of the user and comprises a first side and a second side, and wherein, during operation, said first side of said at least one fluid-actuated massage element for shoulder massaging is in contact with a corresponding shoulder of the user.

30. The massage chair according to claim 24, further comprising a right side and a left side, and wherein said at least one arm massage system is a right arm massage system and a left arm massage system.

31. The massage chair according to claim 24, further comprising a thigh body area portion, wherein said thigh body area portion is located forward of said seat, wherein said body massage system comprises at least one massage element for body massaging, and wherein, during operation, said at least one massage element for body massaging provides massaging effects to at least a back body area of the user.

32. The massage chair according to claim 31, wherein said at least one massage element for body massaging is at least one fluid massage element, and wherein said body massage system further comprises at least one fluid valve device for regulating fluid flow into and out of said at least one fluid massage element, and at least one fluid transport device for transporting fluid flow into and out of said at least one fluid massage element.

33. The massage chair according to claim 31, further comprising a legs and feet massage system and a pair of guide rails, wherein said legs and feet massage system comprises at least one massage element for legs and feet massaging, wherein each of said pair of guide rails comprises a guide channel, wherein said guide channel comprises a plurality of gear teeth, and wherein during operation said at least one massage element for body massaging travels along said guide channel from said body to said seat and vice versa.

34. The massage chair according to claim 24, wherein said body of said massage chair comprises a backrest.

35. The massage chair according to claim 34, wherein said body of said massage chair comprises an armrest and a footrest.

36. The massage chair according to claim 24, wherein said body of said massage chair comprises a footrest.

37. The massage chair according to claim 24, wherein said device for adjusting position of said at least one fluid-actuated massage element for shoulder massaging is movable along at least two axes selected from the group consisting of an x axis, a y axis, and a z axis.

38. The massage chair according to claim 24, wherein at least one of said at least one arm massage system further comprises at least one massage element for hand massaging, and wherein, during operation, said at least one massage element for hand massaging provides massaging effects to a corresponding hand of the user.

39. The massage chair according to claim 38, further comprising a massage chair frame and a device for securing said at least one arm massage system about said massage chair frame, wherein said at least one arm massage system is secured about said massage chair frame.

40. The massage chair according to claim 24, further comprising a massage chair frame and a device for securing said at least one arm massage system about said massage chair frame, wherein said at least one arm massage system is secured about said massage chair frame.

41. The massage chair according to claim 40, wherein said massage chair frame comprises a right side and a left side, wherein said at least one arm massage system is a right arm massage system and a left arm massage system, and wherein said device for securing said at least one arm massage system is a first device for securing said right arm massage system to said right side of said massage chair frame and is a second device for securing said left arm massage system to said left side of said massage chair frame.

42. The massage chair according to claim 40, further comprising a legs and feet frame and a legs and feet massage system, wherein said legs and feet massage system comprises at least one massage element for legs and feet massaging, wherein said massage chair frame further comprises a pair of guide rails, wherein each of said pair of guide rails comprises a guide channel, wherein said guide channel comprises a plurality of gear teeth, and wherein during operation said at least one massage element for body massaging travels along said guide channel from said body to said seat and vice versa.

43. The massage chair according to claim 24, further comprising a noise-reducing, enclosure device that comprises an enclosure housing, an inner surface, an outer surface, and at least an air channel going through said outer surface of said enclosure device.

44. A massage chair comprising:
a massage chair frame comprising a pair of guide rails and a pair of guide channels that are spaced apart to provide a balanced movement of a body massage device along said pair of guide channels,
wherein each of said pair of guide rails comprises a seat body area portion and a back body area portion extending upward from said seat body area portion, and
wherein each of said pair of guide channels comprises a plurality of gear teeth from said back body area portion to said seat body area portion; and
at least one arm massage system comprising at least one fluid-actuated massage element for shoulder massaging and a device for adjusting position of said at least fluid-actuated one massage element for shoulder massaging,
wherein said device for adjusting position of said at least one fluid-actuated massage element for shoulder massaging comprises a first portion, a second portion, and a rotatable mechanical joint,
wherein said first portion of said device for adjusting position of said at least one fluid-actuated massage element for shoulder massaging is stationary and mounted to said body of said massage chair, and
wherein said second portion of said device for adjusting position of said at least one fluid-actuated massage element for shoulder massaging is rotatable on said first portion of said device for adjusting position of said at least one fluid-actuated massage element for shoulder massaging via said rotatable mechanical joint around an axis for accommodating body length and body size of a user.

45. The massage chair according to claim 44, wherein said body massage device is comprised of at least one massage element for body massaging and a guide rail engagement device, wherein said guide rail engagement device is comprised of at least one circular gear with a plurality of gear teeth spaced around a gear body, and wherein said at least one circular gear is mounted on at least one rotation shaft and driven by at least one motor.

46. The massage chair according to claim 45, wherein said at least one massage element of said body massage device is configured to provide massaging effects to a bottom body area and a back body area of the user as said body massage device is temporarily held in place or is being moved along each of said pair of guide channel.

47. The massage chair according to claim 46, wherein said body massage device further comprises at least a rack and pinion system to provide movement for said at least one massage element in three-dimensional directions, and wherein said movement for said at least one massage element of said body massage device in three-dimensional directions is driven by a motor.

48. The massage chair according to claim 45, wherein said at least one massage element of said body massage device is at least one fluid massage element, and wherein said body massage system further comprises at least one fluid valve device for regulating fluid flow into and out of said at least one fluid massage element, and at least one fluid transport device for transporting fluid flow into and out of said at least one fluid massage element.

49. The massage chair according to claim 44, wherein said at least one fluid-actuated massage element for shoulder massaging is configured to be adjacent to the body of the user and comprises a first side and a second side, and wherein, during operation, said first side of said at least one fluid-actuated massage element for shoulder massaging is in contact with a corresponding shoulder of the user.

50. The massage chair according to claim 44, wherein said at least one fluid-actuated massage element for shoulder massaging is selected from the group consisting of an air cell, an air bag, a liquid cell, a liquid bag, a gel cell, a gel bag, and any combination thereof.

51. The massage chair according to claim 44, wherein said at least one arm massage system further comprises at least one massage element for hand massaging, and wherein, during operation, said at least one massage element for hand massaging provides massaging effects to a corresponding hand of the user.

52. The massage chair according to claim 44, further comprising an enclosure housing that encloses at least an air compressor for operational noise reduction.

53. The massage chair according to claim 44, further comprising an enclosure housing that encloses at least an air valve for operational noise reduction.

54. The massage chair according to claim 44, wherein said device for adjusting position of said at least one fluid-actuated massage element for shoulder massaging is movable along at least two axes selected from the group consisting of an x axis, a y axis, and a z axis.

* * * * *